(12) United States Patent
Baker-Glenn et al.

(10) Patent No.: US 9,212,186 B2
(45) Date of Patent: Dec. 15, 2015

(54) BICYCLIC PYRAZOLE LRRK2 SMALL MOLECULE INHIBITORS

(71) Applicant: Genentech, Inc., South San Francisco, CA (US)

(72) Inventors: Charles Baker-Glenn, St. Neots (GB); Bryan K. Chan, San Carlos, CA (US); Jennafer Dotson, Belmont, CA (US); Anthony Estrada, San Carlos, CA (US); Timothy Heffron, Burlingame, CA (US); Joseph Lyssikatos, Piedmont, CA (US); Zachary Sweeney, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/531,349

(22) Filed: Nov. 3, 2014

(65) Prior Publication Data
US 2015/0051201 A1   Feb. 19, 2015

Related U.S. Application Data

(63) Continuation of application No. PCT/EP2013/058942, filed on Apr. 30, 2013.

(60) Provisional application No. 61/642,022, filed on May 3, 2012.

(51) Int. Cl.
| | |
|---|---|
| A61K 31/506 | (2006.01) |
| C07D 487/04 | (2006.01) |
| C07D 471/04 | (2006.01) |
| C07D 498/04 | (2006.01) |
| C07D 498/20 | (2006.01) |
| C07D 491/04 | (2006.01) |
| C07D 403/12 | (2006.01) |
| C07D 491/048 | (2006.01) |

(52) U.S. Cl.
CPC ............ *C07D 487/04* (2013.01); *C07D 471/04* (2013.01); *C07D 498/04* (2013.01); *C07D 498/20* (2013.01); *A61K 31/506* (2013.01); *C07D 403/12* (2013.01); *C07D 491/04* (2013.01); *C07D 491/048* (2013.01)

(58) Field of Classification Search
CPC .............. C07D 403/12; C07D 487/04; C07D 491/048; C07D 491/052; C07D 491/04; A61K 31/506
USPC .......................................... 544/295; 514/275
See application file for complete search history.

(56) References Cited

U.S. PATENT DOCUMENTS

| | | | |
|---|---|---|---|
| 8,796,296 B2* | 8/2014 | Baker-Glenn et al. | 514/272 |
| 8,815,882 B2* | 8/2014 | Baker-Glenn et al. | 514/272 |
| 2007/0191344 A1* | 8/2007 | Choidas et al. | 514/217.06 |
| 2011/0224197 A1* | 9/2011 | Henkel et al. | 514/228.2 |
| 2012/0157427 A1* | 6/2012 | Baker-Glenn et al. | 514/210.2 |
| 2012/0329784 A1* | 12/2012 | Kallander et al. | 514/218 |
| 2013/0045955 A1* | 2/2013 | Bennett et al. | 514/171 |
| 2013/0156700 A1* | 6/2013 | Marik et al. | 424/1.89 |
| 2013/0157999 A1* | 6/2013 | Baker-Glenn et al. | 514/210.18 |
| 2013/0158006 A1* | 6/2013 | Baker-Glenn et al. | 514/211.05 |
| 2013/0158032 A1* | 6/2013 | Baker-Glenn et al. | 514/235.8 |
| 2013/0158057 A1* | 6/2013 | Baker-Glenn et al. | 514/275 |
| 2013/0203755 A1* | 8/2013 | Gelbard et al. | 514/234.2 |
| 2014/0357612 A1* | 12/2014 | Zhang et al. | 514/210.2 |
| 2015/0051238 A1* | 2/2015 | Baker-Glenn et al. | 514/275 |

FOREIGN PATENT DOCUMENTS

WO   WO 2007035309 A1 *  3/2007

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*

B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*

* cited by examiner

*Primary Examiner* — Alexander R Pagano
(74) *Attorney, Agent, or Firm* — Robert C. Hall

(57) ABSTRACT

Compounds of formula I:

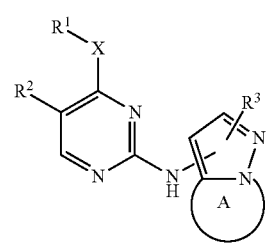

or pharmaceutically acceptable salts thereof,
wherein X, $R^1$, $R^2$, $R^3$ and A are as defined herein. Also disclosed are methods of making the compounds and using the compounds for treatment of diseases associated with LRRK2 receptor, such as Parkinson's disease.

18 Claims, No Drawings

BICYCLIC PYRAZOLE LRRK2 SMALL MOLECULE INHIBITORS

CROSS REFERENCE TO RELATED APPLICATIONS

This application is a continuation of PCT/EP2013/058942 filed on Apr. 30, 2013, which claims priority to U.S. Provisional Application No. 61/642,022 filed May 3, 2012, the disclosures of which are incorporated herein by reference in their entirety.

FIELD OF THE INVENTION

This invention pertains to compounds that modulate the function of LRRK2 and are useful for treatment of LRRK2-mediated diseases and conditions such as Parkinson's disease.

BACKGROUND OF THE INVENTION

Neurodegenerative diseases such as Parkinson's disease, Lewy body dementia and Huntington's disease affect millions of individuals. Parkinson's disease is a chronic, progressive motor system disorder that afflicts approximately one out of every 1000 people, with hereditary Parkinson's disease accounting for 5-10% of all of patients. Parkinson's disease is caused by progressive loss of mid-brain dopamine neurons, leaving patients with impaired ability to direct and control their movements. The primary Parkinson's disease symptoms are trembling, rigidity, slowness of movement, and impaired balance. Many Parkinson's disease patients also experience other symptoms such as emotional changes, memory loss, speech problems, and sleeping disorders.

The gene encoding the leucine-rich repeat kinase 2 protein (LRRK2) has been identified in association with hereditary Parkinson's disease (Paisan-Ruiz et al., *Neuron*, Vol. 44(4), 2004, pp 595-600; Zimprich et al., *Neuron*, Vol. 44(4), 2004, 601-607). In-vitro studies show that Parkinson's disease-associated mutation leads to increased LRRK2 kinase activity and decreased rate of GTP hydrolysis compared to wild-type (Guo et al., *Experimental Cell Research*, Vol. 313(16), 2007, pp. 3658-3670. Anti-LRRK2 antibodies have been used to label brainstem Lewy bodies associated with Parkinson's disease and cortical antibodies associated with Lewis body-dementia suggesting that LRRK2 may play an important role in Lewie body formation and pathogenesis associated with these diseases (Zhou et al., *Molecular Degeneration*, 2006, 1:17 doi:10.1186/1750-1326-1-17). LRRK2 has also been identified as a gene potentially associated with increased susceptibility to Crohn's disease and susceptibility to leprosy (Zhang et al., *New England J. Med.* Vol. 361 (2009) pp. 2609-2618.

LRRK2 has also been associated with the transition of mild cognitive impairment to Alzheimer's disease (WO2007/149789); L-Dopa induced dyskinesia (Hurley et al., *Eur. J. Neurosci.*, Vol. 26, 2007, pp. 171-177; CNS disorders associated with neuronal progenitor differentiation (Milosevic et al., *Neurodegen.*, Vol. 4, 2009, p. 25); cancers such as kidney, breast, prostate, blood and lung cancers and acute myelogenous leukemia (WO2011/038572); papillary renal and thyroid carcinomas (Looyenga et al., www.pnas.org/cgi/doi/10.1073/pnas.1012500108); multiple myeloma (Chapman et al., *Nature* Vol. 471, 2011, pp. 467-472); amyotrophic lateral sclerosis (Shtilbans et al., *Amyotrophic Lateral Sclerosis* "Early Online 2011, pp. 1-7); rheumatoid arthritis (Nakamura et al., *DNA Res.* Vol. 13(4), 2006, pp. 169-183); and ankylosing spondylytis (Danoy et al., *PLoS Genetics*, Vol. 6(12), 2010, e1001195, pp. 1-5).

Accordingly, compounds and compositions effective at modulating LRRK2 activity may provide a treatment for neurodegenerative diseases such as Parkinson's disease and Lewie body dementia, for CNS disorders such as Alzheimer's disease and L-Dopa induced dyskinesia, for cancers such as kidney, breast, prostate, blood, papillary and lung cancers, acute myelogenous leukemia and multiple myeloma, and for inflammatory diseases such as leprosy, Crohn's disease, amyotrophic lateral sclerosis, rheumatoid arthritis, and ankylosing spondylytis. Particularly, there is a need for compounds with LRRK2 affinity that are selective for LRRK2 over other kinases, such as JAK2, which can provide effective drugs for treatment of neurodegenerative disorders such as PD.

SUMMARY OF THE INVENTION

The invention provides compounds of the formula I:

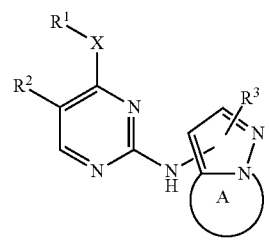

or a pharmaceutically acceptable salt thereof,
wherein:
X is: —$NR^a$—; or —O— wherein $R^a$ is hydrogen or $C_{1-6}$alkyl;
$R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted one or more times with $C_{1-6}$alkyl; $C_{3-6}$cycloalkyl-$C_{1-6}$alkyl wherein the $C_{3-6}$cycloalkyl portion is optionally substituted one or more times with $C_{1-6}$alkyl; heterocyclyl optionally substituted one or more times with $R^5$; or heterocyclyl-$C_{1-6}$alkyl optionally substituted one or more times with $R^5$;
or X and $R^1$ together form $C_{1-6}$alkyl; $C_{1-6}$alkoxy-$C_{1-6}$alkyl; $C_{3-6}$cycloalkyl optionally substituted one or more times with $R^4$; or $C_{3-6}$cycloalkyl-$C_{1-6}$alkyl wherein the $C_{3-6}$cycloalkyl portion is optionally substituted one or more times with $R^4$;
or $R^1$ and $R^a$ together with the atoms to which they are attached may form a three- to six-membered heterocyclic ring optionally substituted one or more times with $R^5$;
$R^2$ is: $C_{1-6}$alkyl; halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$cycloalkyl optionally substituted one or more times with $R^4$; $C_{3-6}$cycloalkyl-$C_{1-6}$alkyl wherein the $C_{3-6}$cycloalkyl portion is optionally substituted one or more times with $R^4$; —$OR^b$ wherein $R^b$ is $C_{1-6}$alkyl, $C_{3-6}$cycloalkyl optionally substituted one or more times with $R^4$, or $C_{3-6}$cycloalkyl-$C_{1-6}$alkyl wherein the $C_{3-6}$cycloalkyl portion is optionally substituted one or more times with $R^4$; or —C(O)—$R^c$ wherein $R^c$ is $C_{1-6}$alkyl, $C_{1-6}$alkoxy, amino, or heterocyclyl optionally substituted one or more times with $R^5$;

$R^3$ is: hydrogen; $C_{1-6}$alkyl; halo; cyano; halo-$C_{1-6}$alkyl; $C_{2-6}$alkenyl; $C_{2-6}$alkynyl; $C_{1-6}$alkoxy; $C_{1-6}$alkoxy-$C_{1-6}$alkyl; hydroxy-$C_{1-6}$alkyl; $C_{3-6}$cycloalkyl optionally substituted one or more times with $R^4$; $C_{3-6}$cycloalkyl-$C_{1-6}$alkyl wherein the $C_{3-6}$cycloalkyl portion is optionally substituted one or more times with $R^4$; or —Y—C(O)—$R^d$;

Y is $C_{2-6}$alkylene or a bond;

$R^d$ is $C_{1-6}$alkyl, $C_{1-6}$alkoxy, amino, $C_{1-6}$alkyl-amino, di-$C_{1-6}$alkyl-amino, halo-$C_{1-6}$alkyl-amino, di-halo-$C_{1-6}$alkyl-amino, halo-$C_{1-6}$alkyl, hydroxy-$C_{1-6}$alkyl, hydroxy, $C_{1-6}$alkoxy-$C_{1-6}$alkyl, cyano-$C_{1-6}$alkyl, $C_{1-6}$alkylsulfonyl$C_{1-6}$alkyl, amino-$C_{1-6}$alkyl, $C_{3-6}$cycloalkyl optionally substituted one or more times with $R^4$, $C_{3-6}$cycloalkyl-$C_{1-6}$alkyl wherein the $C_{3-6}$cycloalkyl portion is optionally substituted one or more times with $R^4$, heterocyclyl optionally substituted one or more times with $R^5$, or heterocyclyl-$C_{1-6}$alkyl wherein the heterocyclyl portion is optionally substituted one or more times with $R^5$;

each $R^4$ is independently: $C_{1-6}$alkyl; halo-$C_{1-6}$alkyl; $C_{1-6}$alkoxy; oxo; cyano; halo; or Y—C(O)—$R^d$;

each $R^5$ is independently: $C_{1-6}$alkyl; halo-$C_{1-6}$alkyl; halo; oxo; $C_{1-6}$alkoxy; $C_{1-6}$alkylsulfonyl; $C_{1-6}$alkoxy-$C_{1-6}$alkyl; cyano; —Y—C(O)—$R^d$; heterocyclyl; heterocyclyl-$C_{1-6}$alkyl; $C_{3-6}$cycloalkyl; $C_{3-6}$cycloalkyl-$C_{1-6}$alkyl; or $C_{3-6}$cycloalkylsulfonyl;

A is a five- or six-membered unsaturated or saturated carbocyclic ring that may may optionally contain a heteroatom selected from O, N and S, and which may be substituted one or more times with $R^6$; and each $R^6$ is independently: oxo; $C_{1-6}$alkyl; halo-$C_{1-6}$alkyl; $C_{1-6}$alkoxy; $C_{1-6}$alkoxy-$C_{1-6}$alkyl; cyano; cyano-$C_{1-6}$alkyl; —Y—C(O)—$R^d$; $C_{3-6}$cycloalkyl, heterocyclyl; or $C_{3-6}$cycloalkyl-$C_{1-6}$alkyl.

The invention also provides pharmaceutical compositions comprising the compounds, methods of using the compounds, and methods of preparing the compounds.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy' means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —$SO_2$—R, wherein R is alkyl as defined herein.

"Alkylsulfonylalkyl means a moiety of the formula —R'—$SO_2$—R" where where R' is alkylene and R" is alkyl as defined herein.

"Alkylsulfonylalkoxy" means a group of the formula —O—R—$SO_2$—R' wherein R is alkylene and R' is alkyl as defined herein.

"Amino means a moiety of the formula —NRR' wherein R and R' each independently is hydrogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

"Arylalkyl" and "Aralkyl", which may be used interchangeably, mean a radical-R$^a$R$^b$ where R$^a$ is an alkylene group and R$^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" "means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, amino sulfonylmethyl, aminosulfonylethyl, amino sulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each optionally substituted.

Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R"' wherein R', R" and R"' each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R"' each independently is hydrogen or alkyl.

"Optionally substituted", when used in association with "aryl", "phenyl", "heteroaryl" "cycloalkyl" or "heterocyclyl", means an aryl, phenyl, heteroaryl, cycloalkyl or heterocyclyl which is optionally substituted independently with one to four substituents, for example one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —SO$_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain particular optional substituents for "aryl", phenyl", "heteroaryl" "cycloalkyl" or "heterocyclyl" include alkyl, halo, haloalkyl, alkoxy, cyano, amino and alkylsulfonyl. In one embodiment substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Parkinson's disease" means a degenerative disorder of the central nervous system that impairs motor skills, speech, and/or cognitive function. Symptoms of Parkinson's disease may include, for example, muscle rigidity, tremor, slowing of physical movement (bradykinesia) and loss of physical movement (akinesia).

"Lewie (Lewy) body disease" also called "Lewie body dementia", diffuse Lewie body disease", cortical Lewie body disease", means a neurogenerative disorder characterized anatomically by the presence of Lewie bodies in the brain.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where one or more chiral centers exists in a structure but no specific stereochemistry is shown for the chiral centers, both enantiomers associated with each such chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes.

Compounds of the Invention

The invention provides compounds of the formula I:

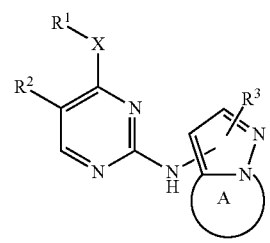

I or a pharmaceutically acceptable salt thereof,
wherein:
X is: —$NR^a$—; or —O— wherein $R^a$ is hydrogen or $C_{1-6}$alkyl;
$R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted one or more times with $C_{1-6}$alkyl; $C_{3-6}$cycloalkyl-$C_{1-6}$alkyl wherein the $C_{3-6}$cycloalkyl portion is optionally substituted one or more times with $C_{1-6}$alkyl; heterocyclyl optionally substituted one or more times with $R^5$; or heterocyclyl-$C_{1-6}$alkyl optionally substituted one or more times with $R^5$;
or X and $R^1$ together form $C_{1-6}$alkyl; $C_{1-6}$alkoxy-$C_{1-6}$alkyl; $C_{3-6}$cycloalkyl optionally substituted one or more times with R⁴; or C₃₋₆cycloalkyl-C₁₋₆alkyl wherein the C₃₋₆cycloalkyl portion is optionally substituted one or more times with R⁴;

or R¹ and Rᵃ together with the atoms to which they are attached may form a three- to six-membered heterocyclic ring optionally substituted one or more times with R⁵;

R² is: C₁₋₆alkyl; halo; C₁₋₆alkoxy; cyano; C₂₋₆alkynyl; C₂₋₆alkenyl; halo-C₁₋₆alkyl; halo-C₁₋₆alkoxy; C₃₋₆cycloalkyl optionally substituted one or more times with R⁴; C₃₋₆cycloalkyl-C₁₋₆alkyl wherein the C₃₋₆cycloalkyl portion is optionally substituted one or more times with R⁴; —ORᵇ wherein Rᵇ is C₁₋₆alkyl, C₃₋₆cycloalkyl optionally substituted one or more times with R⁴, or C₃₋₆cycloalkyl-C₁₋₆alkyl wherein the C₃₋₆cycloalkyl portion is optionally substituted one or more times with R⁴; or —C(O)—Rᶜ wherein Rᶜ is C₁₋₆alkyl, C₁₋₆alkoxy, amino, or heterocyclyl optionally substituted one or more times with R⁵;

R³ is: hydrogen; C₁₋₆alkyl; halo; cyano; halo-C₁₋₆alkyl; C₂₋₆alkenyl; C₂₋₆alkynyl; C₁₋₆alkoxy; C₁₋₆alkoxy-C₁₋₆alkyl; hydroxy-C₁₋₆alkyl; C₃₋₆cycloalkyl optionally substituted one or more times with R⁴; C₃₋₆cycloalkyl-C₁₋₆alkyl wherein the C₃₋₆cycloalkyl portion is optionally substituted one or more times with R⁴; or —Y—C(O)—Rᵈ;

Y is C₂₋₆alkylene or a bond;

Rᵈ is C₁₋₆alkyl, C₁₋₆alkoxy, amino, C₁₋₆alkyl-amino, di-C₁₋₆alkyl-amino, halo-C₁₋₆alkyl-amino, di-halo-C₁₋₆alkyl-amino, halo-C₁₋₆alkyl, hydroxy-C₁₋₆alkyl, hydroxy, C₁₋₆alkoxy-C₁₋₆alkyl, cyano-C₁₋₆alkyl, C₁₋₆alkylsulfonylC₁₋₆alkyl, amino-C₁₋₆alkyl, C₃₋₆cycloalkyl optionally substituted one or more times with R⁴, C₃₋₆cycloalkyl-C₁₋₆alkyl wherein the C₃₋₆cycloalkyl portion is optionally substituted one or more times with R⁴, heterocyclyl optionally substituted one or more times with R⁵, or heterocyclyl-C₁₋₆alkyl wherein the heterocyclyl portion is optionally substituted one or more times with R⁵;

each R⁴ is independently: C₁₋₆alkyl; halo-C₁₋₆alkyl; C₁₋₆alkoxy; oxo; cyano; halo; or Y—C(O)—Rᵈ;

each R⁵ is independently: C₁₋₆alkyl; halo-C₁₋₆alkyl; halo; oxo; C₁₋₆alkoxy; C₁₋₆alkylsulfonyl; C₁₋₆alkoxy-C₁₋₆alkyl; cyano; —Y—C(O)—Rᵈ; heterocyclyl; heterocyclyl-C₁₋₆alkyl; C₃₋₆cycloalkyl; C₃₋₆cycloalkyl-C₁₋₆alkyl; or C₃₋₆cycloalkylsulfonyl;

A is a five- or six-membered unsaturated or saturated carbocyclic ring that may may optionally contain a heteroatom selected from O, N and S, and which may be substituted one or more times with R⁶; and each R⁶ is independently: oxo; C₁₋₆alkyl; halo-C₁₋₆alkyl; C₁₋₆alkoxy; C₁₋₆alkoxy-C₁₋₆alkyl; cyano; cyano-C₁₋₆alkyl; —Y—C(O)—Rᵈ; C₃₋₆cycloalkyl, heterocyclyl; or C₃₋₆cycloalkyl-C₁₋₆alkyl.

In certain embodiments the invention provides compounds of formula I or a pharmaceutically acceptable salt thereof, wherein X is NH, R¹ is methyl and R² is CF₃.

In certain embodiments the invention provides compounds of formula I or a pharmaceutically acceptable salt thereof, wherein X is NH, R¹ is ethyl and R² is CF₃.

In certain embodiments the invention provides compounds of formula I or a pharmaceutically acceptable salt thereof, wherein X is NH, R¹ is cyclopropyl and R² is CF₃.

In certain embodiments the invention provides compounds of formula IIA or formula IIB:

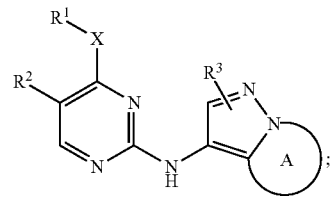

IIA

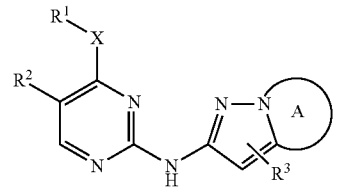

IIB or a pharmaceutically acceptable salt thereof,
wherein X, R¹, R², R³ and A are as defined herein.

In certain embodiments, the compounds are of formula IIA.

In certain embodiments, the compounds are of formula IIB.

In certain embodiments of formula I, formula IIA or formula IIB, X is —NRᵃ— or —O—.

In certain embodiments of formula I, formula IIA or formula IIB, X is —NRᵃ.

In certain embodiments of formula I, formula IIA or formula IIB, X is —O—.

In certain embodiments of formula I, formula IIA or formula IIB, X is —NH— or —O—.

In certain embodiments of formula I, formula IIA or formula IIB, X is —NH—.

In certain embodiments of formula I, formula IIA or formula IIB, X is —O—.

In certain embodiments of formula I, formula IIA or formula IIB, Rᵃ is hydrogen.

In certain embodiments of formula I, formula IIA or formula IIB, Rᵃ is C₁₋₆alkyl.

In certain embodiments of formula I, formula IIA or formula IIB, R¹ is: C₁₋₆alkyl; C₂₋₆alkenyl; C₂₋₆alkynyl; halo-C₁₋₆alkyl; C₁₋₆alkoxy-C₁₋₆alkyl; hydroxy-C₁₋₆alkyl; amino-C₁₋₆alkyl; C₁₋₆alkylsulfonyl-C₁₋₆alkyl; C₃₋₆cycloalkyl optionally substituted with C₁₋₆alkyl; C₃₋₆cycloalkyl-C₁₋₆alkyl wherein the C₃₋₆cycloalkyl portion is optionally substituted with C₁₋₆alkyl; heterocyclyl; or heterocyclyl-C₁₋₆alkyl.

In certain embodiments of formula I, formula IIA or formula IIB, R¹ is: C₁₋₆alkyl; halo-C₁₋₆alkyl; C₁₋₆alkoxy-C₁₋₆alkyl; amino-C₁₋₆alkyl; C₁₋₆alkylsulfonyl-C₁₋₆alkyl; C₃₋₆cycloalkyl; or C₃₋₆cycloalkyl-C₁₋₆alkyl.

In certain embodiments of formula I, formula IIA or formula IIB, R¹ is: C₁₋₆alkyl; C₃₋₆cycloalkyl optionally substituted with C₁₋₆alkyl; or C₃₋₆cycloalkyl-C₁₋₆alkyl wherein the C₃₋₆cycloalkyl portion is optionally substituted with C₁₋₆alkyl.

In certain embodiments of formula I, formula IIA or formula IIB, R¹ is: C₁₋₆alkyl; halo-C₁₋₆alkyl; C₁₋₆alkoxy-C₁₋₆alkyl; amino-C₁₋₆alkyl; C₁₋₆alkylsulfonyl-C₁₋₆alkyl; tetrahydrofuranyl; tetrahydrofuranyl-C₁₋₆alkyl; oxetanyl; or oxetan-C₁₋₆alkyl.

In certain embodiments of formula I, formula IIA or formula IIB, R¹ is: C₁₋₆alkyl; halo-C₁₋₆alkyl; C₁₋₆alkoxy-C₁₋₆alkyl; amino-C₁₋₆alkyl; or C₁₋₆alkylsulfonyl-C₁₋₆alkyl.

In certain embodiments of formula I, formula IIA or formula IIB, $R^1$ is $C_{1-6}$alkyl or halo-$C_{1-6}$alkyl.

In certain embodiments of formula I, formula IIA or formula IIB, $R^1$ is $C_{1-6}$alkyl.

In certain embodiments of formula I, formula IIA or formula IIB, $R^1$ is halo-$C_{1-6}$alkyl.

In certain embodiments of formula I, formula IIA or formula IIB, $R^1$ is $C_{1-6}$alkoxy-$C_{1-6}$alkyl.

In certain embodiments of formula I, formula IIA or formula IIB, $R^1$ is amino-$C_{1-6}$alkyl.

In certain embodiments of formula I, formula IIA or formula IIB, $R^1$ is $C_{1-6}$alkylsulfonyl-$C_{1-6}$alkyl.

In certain embodiments of formula I, formula IIA or formula IIB, $R^1$ is $C_{3-6}$cycloalkyl optionally substituted with $C_{1-6}$alkyl.

In certain embodiments of formula I, formula IIA or formula IIB, $R^1$ is $C_{3-6}$cycloalkyl-$C_{1-6}$alkyl wherein the $C_{3-6}$cycloalkyl portion is optionally substituted with $C_{1-6}$alkyl.

In certain embodiments of formula I, formula IIA or formula IIB, $R^1$ is heterocyclyl or heterocyclyl-$C_{1-6}$alkyl.

In embodiments of formula I, formula IIA or formula IIB wherein $R^1$ is heterocyclyl or heterocyclyl-$C_{1-6}$alkyl, such heterocyclyl may be piperidinyl, piperazinyl, morpholinyl, tetrahydropyranyl, pyrrolidinyl, tetrahydrofuranyl or oxetanyl, each optionally substituted as defined herein.

In embodiments of formula I, formula IIA or formula IIB wherein $R^1$ is heterocyclyl or heterocyclyl-$C_{1-6}$alkyl, such heterocyclyl may be tetrahydropyranyl, piperidinyl, tetrahydrofuranyl or oxetanyl, each optionally substituted as defined herein.

In certain embodiments of formula I, formula IIA or formula IIB, $R^1$ is tetrahydrofuranyl.

In certain embodiments of formula I, formula IIA or formula IIB, $R^1$ is tetrahydropyranyl.

In certain embodiments of formula I, formula IIA or formula IIB, $R^1$ is tetrahydrofuranyl-$C_{1-6}$alkyl or oxetanyl.

In certain embodiments of formula I, formula IIA or formula IIB, $R^1$ is tetrahydrofuranyl-$C_{1-6}$alkyl.

In certain embodiments of formula I, formula IIA or formula IIB, $R^1$ is oxetanyl.

In certain embodiments of formula I, formula IIA or formula IIB, $R^1$ is or oxetan-$C_{1-6}$alkyl.

In certain embodiments of formula I, formula IIA or formula IIB, $R^1$ is: methyl; ethyl; n-propyl; isopropyl; isobutyl; 3,3-dimethylpropyl; cyclopropyl; cyclobutyl; cyclopentyl; cyclohexyl; cyclopropylmethyl; cyclobutylmethyl; cyclopentylmethyl; cyclopropylethyl; methoxyethyl; oxetanyl; tetrahydropyranyl; 2,2-difluoroethyl; or tetrahydrofuranylmethyl.

In certain embodiments of formula I, formula IIA or formula IIB, $R^1$ is: methyl; ethyl; n-propyl; isopropyl; isobutyl; 3,3-dimethylpropyl; cyclopentyl; cyclohexyl; cyclopropylmethyl; cyclobutylmethyl; cyclopentylmethyl; cyclopropylethyl; methoxyethyl; oxetanyl; tetrahydropyranyl; 2,2-difluoroethyl; or tetrahydrofuranylmethyl.

In certain embodiments of formula I, formula IIA or formula IIB, $R^1$ is: methyl; ethyl; n-propyl; isopropyl; isobutyl; 3,3-dimethylpropyl; cyclopentyl; cyclohexyl; cyclopentylmethyl; methoxyethyl; oxetanyl; tetrahydropyranyl; or tetrahydrofuranylmethyl.

In certain embodiments of formula I, formula IIA or formula IIB, $R^1$ is 2,2-difluoroethyl.

In certain embodiments of formula I, formula IIA or formula IIB, $R^1$ is: methyl; ethyl; n-propyl; isopropyl; or isobutyl.

In certain embodiments of formula I, formula IIA or formula IIB, $R^1$ is methyl, ethyl or cyclopropyl.

In certain embodiments of formula I, formula IIA or formula IIB, $R^1$ is methyl or ethyl.

In certain embodiments of formula I, formula IIA or formula IIB, $R^1$ is methyl.

In certain embodiments of formula I, formula IIA or formula IIB, $R^1$ is ethyl.

In certain embodiments of formula I, formula IIA or formula IIB, $R^1$ is: cyclopropyl; cyclobutyl; cyclopentyl; cyclohexyl; cyclopropylmethyl; cyclobutylmethyl; cyclopentylmethyl; or cyclopropylethyl.

In certain embodiments of formula I, formula IIA or formula IIB, $R^1$ is: cyclopentyl; cyclohexyl; or cyclopentylmethyl.

In certain embodiments of formula I, formula IIA or formula IIB, $R^1$ is: cyclopropyl.

In certain embodiments of formula I, formula IIA or formula IIB, $R^1$ and $R^a$ together with the atoms to which they are attached may form a three- to six-membered heterocyclic ring.

In certain embodiments of formula I, formula IIA or formula IIB, $R^1$ and $R^a$ together with the atoms to which they are attached may form a three-membered heterocyclic ring.

In certain embodiments of formula I, formula IIA or formula IIB, $R^1$ and $R^a$ together with the atoms to which they are attached may form a four-membered heterocyclic ring.

In certain embodiments of formula I, formula IIA or formula IIB, $R^1$ and $R^a$ together with the atoms to which they are attached may form a five-membered heterocyclic ring.

In certain embodiments of formula I, formula IIA or formula IIB, $R^1$ and $R^a$ together with the atoms to which they are attached may form a six-membered heterocyclic ring.

In certain embodiments of formula I, formula IIA or formula IIB, X and $R^1$ together form $C_{1-6}$alkyl; $C_{3-6}$cycloalkyl optionally substituted with $C_{1-6}$alkyl; or $C_{3-6}$cycloalkyl-$C_{1-6}$alkyl wherein the $C_{3-6}$cycloalkyl portion is optionally substituted with $C_{1-6}$alkyl.

In certain embodiments of formula I, formula IIA or formula IIB, X and $R^1$ together form $C_{1-6}$alkyl.

In certain embodiments of formula I, formula IIA or formula IIB, X and $R^1$ together form $C_{3-6}$cycloalkyl optionally substituted with $C_{1-6}$alkyl.

In certain embodiments of formula I, formula IIA or formula IIB, X and $R^1$ together form $C_{3-6}$cycloalkyl-$C_{1-6}$alkyl wherein the $C_{3-6}$cycloalkyl portion is optionally substituted with $C_{1-6}$alkyl.

In certain embodiments of formula I, formula IIA or formula IIB, $R^2$ is: $C_{1-6}$alkyl; halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; —$OR^b$ wherein $R^b$ is $C_{1-6}$alkyl, $C_{3-6}$cycloalkyl optionally substituted with $C_{1-6}$alkyl, or $C_{3-6}$cycloalkyl-$C_{1-6}$alkyl wherein the $C_{3-6}$cycloalkyl portion is optionally substituted with $C_{1-6}$alkyl; or —C(O)—$R^c$.

In certain embodiments of formula I, formula IIA or formula IIB, $R^2$ is: halo; $C_{1-6}$alkoxy; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; oxetanyl; or oxetan-$C_{1-6}$alkyl.

In certain embodiments of formula I, formula IIA or formula IIB, $R^2$ is: halo; $C_{1-6}$alkoxy; halo-$C_{1-6}$alkyl; cyano; $C_{2-6}$alkynyl; $C_{2-6}$alkenyl; $C_{3-6}$cycloalkyl; or $C_{3-6}$cycloalkyl-$C_{1-6}$alkyl.

In certain embodiments of formula I, formula IIA or formula IIB, $R^2$ is: halo; $C_{1-6}$alkoxy; halo-$C_{1-6}$alkyl; cyano; $C_{3-6}$cycloalkyl; or $C_{3-6}$cycloalkyl-$C_{1-6}$alkyl.

In certain embodiments of formula I, formula IIA or formula IIB, $R^2$ is: halo; $C_{1-6}$alkoxy; halo-$C_{1-6}$alkyl; $C_{3-6}$cycloalkyl; or $C_{3-6}$cycloalkyl-$C_{1-6}$alkyl.

In certain embodiments of formula I, formula IIA or formula IIB, $R^2$ is: halo; halo-$C_{1-6}$alkyl or cyano.

In certain embodiments of formula I, formula IIA or formula IIB, $R^2$ is: fluoro; bromo; chloro; iodo; trifluoromethyl; or cyano.

In certain embodiments of formula I, formula IIA or formula IIB, $R^2$ is: chloro; trifluoromethyl; or cyano.

In certain embodiments of formula I, formula IIA or formula IIB, $R^2$ is: halo; or halo-$C_{1-6}$alkyl.

In certain embodiments of formula I, formula IIA or formula IIB, $R^2$ is $C_{1-6}$alkyl.

In certain embodiments of formula I, formula IIA or formula IIB, $R^2$ is halo.

In certain embodiments of formula I, formula IIA or formula IIB, $R^2$ is $C_{1-6}$alkoxy.

In certain embodiments of formula I, formula IIA or formula IIB, $R^2$ is halo-$C_{1-6}$alkoxy.

In certain embodiments of formula I, formula IIA or formula IIB, $R^2$ is halo-$C_{1-6}$alkyl.

In certain embodiments of formula I, formula IIA or formula IIB, $R^2$ is $C_{3-6}$cycloalkyl.

In certain embodiments of formula I, formula IIA or formula IIB, $R^2$ is $C_{3-6}$cycloalkyl-$C_{1-6}$alkyl.

In certain embodiments of formula I, formula IIA or formula IIB, $R^2$ is tetrahydrofuranyl.

In certain embodiments of formula I, formula IIA or formula IIB, $R^2$ is tetrahydrofuranyl-$C_{1-6}$alkyl.

In certain embodiments of formula I, formula IIA or formula IIB, $R^2$ is oxetanyl.

In certain embodiments of formula I, formula IIA or formula IIB, $R^2$ is oxetan-$C_{1-6}$alkyl.

In certain embodiments of formula I, formula IIA or formula IIB, $R^2$ is fluoro, chloro or bromo.

In certain embodiments of formula I, formula IIA or formula IIB, $R^2$ is chloro.

In certain embodiments of formula I, formula IIA or formula IIB, $R^2$ is fluoro.

In certain embodiments of formula I, formula IIA or formula IIB, $R^2$ is bromo.

In certain embodiments of formula I, formula IIA or formula IIB, $R^2$ is bromo.

In certain embodiments of formula I, formula IIA or formula IIB, $R^2$ is iodo.

In certain embodiments of formula I, formula IIA or formula IIB, $R^2$ is trifluoromethyl.

In certain embodiments of formula I, formula IIA or formula IIB, $R^2$ is methoxy.

In certain embodiments of formula I, formula IIA or formula IIB, $R^2$ is cyano.

In certain embodiments of formula I, formula IIA or formula IIB, $R^2$ is $C_{2-6}$alkynyl.

In certain embodiments of formula I, formula IIA or formula IIB, $R^2$ is $C_{2-6}$alkenyl.

In certain embodiments of formula I, formula IIA or formula IIB, $R^2$ is —$OR^b$ wherein $R^b$ is $C_{1-6}$alkyl, $C_{3-6}$cycloalkyl optionally substituted with $C_{1-6}$alkyl, or $C_{3-6}$cycloalkyl-$C_{1-6}$alkyl wherein the $C_{3-6}$cycloalkyl portion is optionally substituted with $C_{1-6}$alkyl.

In certain embodiments of formula I, $R^2$ is —C(O)—$R^c$ wherein $R^c$ is $C_{1-6}$alkyl, $C_{1-6}$alkoxy, amino, or heterocyclyl.

In certain embodiments of formula I, formula IIA or formula IIB, $R^3$ is: hydrogen; $C_{1-6}$alkyl; halo; cyano; halo-$C_{1-6}$alkyl; $C_{2-6}$alkenyl; $C_{2-6}$alkynyl; $C_{1-6}$alkoxy; $C_{1-6}$alkoxy-$C_{1-6}$alkyl; hydroxy-$C_{1-6}$alkyl; $C_{3-6}$cycloalkyl; or $C_{3-6}$cycloalkyl-$C_{1-6}$alkyl.

In certain embodiments of formula I, formula IIA or formula IIB, $R^3$ is: hydrogen; $C_{1-6}$alkyl; halo-$C_{1-6}$alkyl; $C_{3-6}$cycloalkyl; or $C_{3-6}$cycloalkyl-$C_{1-6}$alkyl.

In certain embodiments of formula I, formula IIA or formula IIB, $R^3$ is: hydrogen; $C_{1-6}$alkyl; or $C_{3-6}$cycloalkyl.

In certain embodiments of formula I, formula IIA or formula IIB, $R^3$ is: hydrogen; $C_{1-6}$alkyl; halo; or $C_{3-6}$cycloalkyl optionally substituted with $C_{1-6}$alkyl.

In certain embodiments of formula I, formula IIA or formula IIB, $R^3$ is hydrogen or $C_{1-6}$alkyl.

In certain embodiments of formula I, formula IIA or formula IIB, $R^3$ is hydrogen.

In certain embodiments of formula I, formula IIA or formula IIB, $R^3$ is $C_{1-6}$alkyl.

In certain embodiments of formula I, formula IIA or formula IIB, $R^3$ is halo.

In certain embodiments of formula I, formula IIA or formula IIB, $R^3$ is cyano.

In certain embodiments of formula I, formula IIA or formula IIB, $R^3$ is halo-$C_{1-6}$alkyl.

In certain embodiments of formula I, formula IIA or formula IIB, $R^3$ is $C_{1-6}$alkoxy-$C_{1-6}$alkyl.

In certain embodiments of formula I, formula IIA or formula IIB, $R^3$ is hydroxy-$C_{1-6}$alkyl.

In certain embodiments of formula I, formula IIA or formula IIB, $R^3$ is $C_{3-6}$cycloalkyl optionally substituted with $C_{1-6}$alkyl.

In certain embodiments of formula I, formula IIA or formula IIB, $R^3$ is hydrogen or methyl.

In certain embodiments of formula I, formula IIA or formula IIB, $R^3$ is $C_{3-6}$cycloalkyl-$C_{1-6}$alkyl wherein the $C_{3-6}$cycloalkyl portion is optionally substituted with $C_{1-6}$alkyl.

In certain embodiments of formula I, formula IIA or formula IIB, $R^3$ is —C(O)—$R^c$ wherein $R^c$ is $C_{1-6}$alkyl, $C_{1-6}$alkoxy, amino, or heterocyclyl.

In certain embodiments of formula I, formula IIA or formula IIB, $R^3$ is —C(O)—$R^c$ wherein $R^c$ is heterocyclyl.

In embodiments of formula I, formula IIA or formula IIB wherein $R^c$ is heterocyclyl, such heterocyclyl may be pyrrolidinyl, piperidinyl, piperazinyl or morpholinyl.

In embodiments of formula I, formula IIA or formula IIB wherein $R^c$ is heterocyclyl, such heterocyclyl may be piperidinyl, piperazinyl or morpholinyl.

In certain embodiments of formula I, formula IIA or formula IIB, $R^3$ is: hydrogen; methyl; isopropyl; cyclopropyl; chloro; or morpholin-4-yl-carbonyl.

In certain embodiments of formula I, formula IIA or formula IIB, $R^3$ is: hydrogen; methyl; isopropyl; cyclopropyl; or chloro.

In certain embodiments of formula I, formula IIA or formula IIB, $R^3$ is methyl.

In certain embodiments of formula I, formula IIA or formula IIB, $R^3$ is isopropyl.

In certain embodiments of formula I, formula IIA or formula IIB, $R^3$ is cyclopropyl.

In certain embodiments of formula I, formula IIA or formula IIB, $R^3$ is chloro.

In certain embodiments of formula I, formula IIA or formula IIB, $R^3$ is morpholin-4-yl-carbonyl.

In certain embodiments of formula I, formula IIA or formula IIB, $R^3$ is 2-fluoro-ethyl.

In certain embodiments of formula I, formula IIA or formula IIB, $R^3$ is $C_{3-6}$cycloalkyl optionally substituted one or more times, or one or two times, with $R^4$.

In certain embodiments of formula I, formula IIA or formula IIB, $R^3$ is $C_{3-6}$cycloalkyl-$C_{1-6}$alkyl wherein the $C_{3-6}$cycloalkyl portion is optionally substituted one or more times, or one or two times, with $R^6$.

In certain embodiments of formula I, formula IIA or formula IIB, $R^3$ is —Y—C(O)—$R^d$.

In certain embodiments of formula I, formula IIA or formula IIB, Y is a bond.

In certain embodiments of formula I, formula IIA or formula IIB, Y is $C_{2-6}$alkylene.

In certain embodiments of formula I, formula IIA or formula IIB, Y is isopropylidine.

In certain embodiments of formula I, formula IIA or formula IIB, Y is methylene.

In certain embodiments of formula I, formula IIA or formula IIB, Y is ethylene.

In certain embodiments of formula I, formula IIA or formula IIB, Y is —C(CH$_3$)$_2$—.

In certain embodiments of formula I, formula IIA or formula IIB, Y is —CH$_2$—.

In certain embodiments of formula I, formula IIA or formula IIB, Y is —CH(CH$_3$)—.

In certain embodiments of formula I, formula IIA or formula IIB, Y is —CH$_2$—C(CH$_3$)$_2$—.

In certain embodiments of formula I, formula IIA or formula IIB, Y is —C(CH$_3$)$_2$—CH$_2$—.

In certain embodiments of formula I, formula IIA or formula IIB, $R^d$ is $C_{1-6}$alkyl, $C_{1-6}$alkoxy, amino, or heterocyclyl.

In certain embodiments of formula I, formula IIA or formula IIB, $R^d$ is $C_{1-6}$alkyl.

In certain embodiments of formula I, formula IIA or formula IIB, $R^d$ is $C_{1-6}$alkoxy.

In certain embodiments of formula I, formula IIA or formula IIB, $R^d$ is amino.

In certain embodiments of formula I, formula IIA or formula IIB, $R^d$ is halo-$C_{1-6}$alkyl.

In certain embodiments of formula I, formula IIA or formula IIB, $R^d$ is hydroxy-$C_{1-6}$alkyl.

In certain embodiments of formula I, formula IIA or formula IIB, $R^d$ is $C_{1-6}$alkoxy-$C_{1-6}$alkyl.

In certain embodiments of formula I, formula IIA or formula IIB, $R^d$ is cyano-$C_{1-6}$alkyl.

In certain embodiments of formula I, formula IIA or formula IIB, $R^d$ is $C_{1-6}$alkylsulfonyl$C_{1-6}$alkyl.

In certain embodiments of formula I, formula IIA or formula IIB, $R^d$ is amino-$C_{1-6}$alkyl.

In certain embodiments of formula I, formula IIA or formula IIB, $R^d$ is $C_{3-6}$cycloalkyl optionally substituted one or more times with $R^4$.

In certain embodiments of formula I, formula IIA or formula IIB, $R^d$ is $C_{3-6}$cycloalkyl-$C_{1-6}$alkyl wherein the $C_{3-6}$cycloalkyl portion is optionally substituted one or more times with $R^4$.

In certain embodiments of formula I, formula IIA or formula IIB, $R^d$ is heterocyclyl optionally substituted one or more times with $R^5$.

In certain embodiments of formula I, formula IIA or formula IIB, $R^d$ is heterocyclyl-$C_{1-6}$alkyl wherein the heterocyclyl portion is optionally substituted one or more times with $R^5$.

In certain embodiments of formula I, formula IIA or formula IIB, $R^d$ is 1-methyl-cyclopropyl; methylamino; dimethylamino; pyrrolidin-1-yl; methoxy; cyclopropyl-methyl; ethyl; 2,2,2-trifluoro-ethyl; tert-butyl; or isopropyl.

In certain embodiments of formula I, formula IIA or formula IIB, $R^d$ is 1-methyl-cyclopropyl.

In certain embodiments of formula I, formula IIA or formula IIB, $R^d$ is methylamino.

In certain embodiments of formula I, formula IIA or formula IIB, $R^d$ is dimethylamino.

In certain embodiments of formula I, formula IIA or formula IIB, $R^d$ is pyrrolidin-1-yl.

In certain embodiments of formula I, formula IIA or formula IIB, $R^d$ is methoxy.

In certain embodiments of formula I, formula IIA or formula IIB, $R^d$ is cyclopropyl-methyl.

In certain embodiments of formula I, formula IIA or formula IIB, $R^d$ is ethyl.

In certain embodiments of formula I, formula IIA or formula IIB, $R^d$ is 2,2,2-trifluoro-ethyl.

In certain embodiments of formula I, formula IIA or formula IIB, $R^d$ is tert-butyl.

In certain embodiments of formula I, formula IIA or formula IIB, $R^d$ is isopropyl.

In embodiments of formula I, formula IIA or formula IIB wherein $R^d$ is heterocyclyl or heterocyclyl-$C_{1-6}$alkyl, such heterocyclyl may be piperidinyl, piperazinyl, morpholinyl, tetrahydropyranyl, pyrrolidinyl, azetidinyl, tetrahydrofuranyl or oxetanyl, each optionally substituted one or more times, or one or two times, with $R^5$ as defined herein.

In embodiments of formula I, formula IIA or formula IIB wherein $R^d$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with $R^5$.

In embodiments of formula I, formula IIA or formula JIB wherein $R^d$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with $R^5$.

In certain embodiments of formula I, formula IIA or formula IIB, $R^4$ is $C_{1-6}$alkyl; halo-$C_{1-6}$alkyl; $C_{1-6}$alkoxy; or halo.

In certain embodiments of formula I, formula IIA or formula IIB, $R^4$ is $C_{1-6}$alkyl; halo-$C_{1-6}$alkyl; or halo.

In certain embodiments of formula I, formula IIA or formula IIB, $R^4$ is $C_{1-6}$alkyl.

In certain embodiments of formula I, formula IIA or formula IIB, $R^4$ is halo-$C_{1-6}$alkyl.

In certain embodiments of formula I, formula IIA or formula IIB, $R^4$ is $C_{1-6}$alkoxy.

In certain embodiments of formula I, formula IIA or formula IIB, $R^4$ is cyano.

In certain embodiments of formula I, formula IIA or formula IIB, $R^4$ is halo.

In certain embodiments of formula I, formula IIA or formula IIB, $R^4$ is Y—C(O)—$R^d$.

In certain embodiments of formula I, formula IIA or formula IIB, $R^4$ is oxo.

In certain embodiments of formula I, formula IIA or formula IIB, each $R^5$ is independently $C_{1-6}$alkyl; halo-$C_{1-6}$alkyl; halo; $C_{1-6}$alkylsulfonyl; $C_{1-6}$alkoxy-$C_{1-6}$alkyl; cyano; heterocyclyl; or $C_{3-6}$cycloalkylsulfonyl wherein the $C_{3-6}$cycloalkyl portion is optionally substituted one or more times with $R^6$.

In certain embodiments of formula I, formula IIA or formula IIB, each $R^5$ is independently $C_{1-6}$alkyl; halo-$C_{1-6}$alkyl; or halo.

In certain embodiments of formula I, formula IIA or formula IIB, $R^5$ is $C_{1-6}$alkyl.

In certain embodiments of formula I, formula IIA or formula IIB, $R^5$ is halo-$C_{1-6}$alkyl.

In certain embodiments of formula I, formula IIA or formula IIB, $R^5$ is halo.

In certain embodiments of formula I, formula IIA or formula IIB, $R^5$ is $C_{1-6}$alkylsulfonyl.

In certain embodiments of formula I, formula IIA or formula IIB, $R^5$ is $C_{1-6}$alkoxy-$C_{1-6}$alkyl.

In certain embodiments of formula I, formula IIA or formula IIB, $R^5$ is cyano.

In certain embodiments of formula I, formula IIA or formula IIB, $R^5$ is —Y—C(O)—$R^d$.

In certain embodiments of formula I, formula IIA or formula IIB, $R^5$ is heterocyclyl.

In certain embodiments of formula I, formula IIA or formula IIB, $R^5$ is $C_{3-6}$cycloalkylsulfonyl wherein the $C_{3-6}$cycloalkyl portion is optionally substituted one or more times with $R^6$.

In certain embodiments of formula I, formula IIA or formula IIB, $R^5$ is oxo.

In certain embodiments of formula I, formula IIA or formula IIB, $R^5$ is $C_{1-6}$alkoxy.

In certain embodiments of formula I, formula IIA or formula IIB, $R^5$ is heterocyclyl-$C_{1-6}$alkyl.

In certain embodiments of formula I, formula IIA or formula IIB, $R^5$ is $C_{3-6}$cycloalkyl.

In certain embodiments of formula I, formula IIA or formula IIB, $R^5$ is $C_{3-6}$cycloalkyl-$C_{1-6}$alkyl.

In embodiments of formula I, formula IIA or formula IIB wherein $R^5$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl.

In embodiments of formula I, formula IIA or formula IIB wherein $R^5$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl.

In embodiments of formula I, formula IIA or formula IIB, ring A is a five-membered ring.

In embodiments of formula I, formula IIA or formula IIB, ring A is a six-membered ring.

In embodiments of formula I, formula IIA or formula IIB, ring A is saturated.

In embodiments of formula I, formula IIA or formula IIB, ring A is unsaturated.

In embodiments of formula I, formula IIA or formula IIB, ring A is carbocyclic.

In embodiments of formula I, formula IIA or formula IIB, ring A contains a heteroatom selected from O, N and S.

In embodiments of formula I, formula IIA or formula IIB, ring A contains a heteroatom O.

In embodiments of formula I, formula IIA or formula IIB, ring A contains a heteroatom N.

In embodiments of formula I, formula IIA or formula IIB, ring A contains a heteroatom S.

In embodiments of formula I, formula IIA or formula IIB, ring A is substituted at least once with a group $R^6$.

In embodiments of formula I, formula IIA or formula IIB, ring A is substituted at least once with a group $R^6$.

In embodiments of formula I, formula IIA or formula IIB, ring A is substituted one, two or three times with a group $R^6$.

In embodiments of formula I, formula IIA or formula IIB, ring A is substituted one, two, three or four times with a group $R^6$.

In certain embodiments of formula I, formula IIA or formula IIB, $R^6$ is oxo.

In certain embodiments of formula I, formula IIA or formula IIB, $R^6$ is $C_{1-6}$alkyl.

In certain embodiments of formula I, formula IIA or formula IIB, $R^6$ is methyl.

In certain embodiments of formula I, formula IIA or formula IIB, $R^6$ is halo-$C_{1-6}$alkyl.

In certain embodiments of formula I, formula IIA or formula IIB, $R^6$ is halo.

In certain embodiments of formula I, formula IIA or formula IIB, $R^6$ is $C_{1-6}$alkyl-sulfonyl.

In certain embodiments of formula I, formula IIA or formula IIB, $R^6$ is $C_{1-6}$alkoxy.

In certain embodiments of formula I, formula IIA or formula IIB, $R^6$ is $C_{1-6}$alkoxy-$C_{1-6}$alkyl.

In certain embodiments of formula I, formula IIA or formula IIB, $R^6$ is cyano.

In certain embodiments of formula I, formula IIA or formula IIB, $R^6$ is cyano-$C_{1-6}$alkyl.

In certain embodiments of formula I, formula IIA or formula IIB, $R^6$ is —Y—C(O)—$R^d$.

In certain embodiments of formula I, formula IIA or formula IIB, $R^6$ is $C_{3-6}$cycloalkyl.

In certain embodiments of formula I, formula IIA or formula IIB, $R^6$ is $C_{3-6}$cycloalkyl-$C_{1-6}$alkyl.

In certain embodiments of formula I, formula IIA or formula IIB, $R^6$ is heterocyclyl.

In embodiments of formula I, formula IIA or formula IIB wherein $R^6$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl.

In embodiments of formula I, formula IIA or formula IIB wherein $R^6$ is $C_{3-6}$cycloalkyl or heterocyclyl, such $C_{3-6}$cycloalkyl or heterocyclyl may be joined to ring A either: (a) by a single bond to an atom of ring A; (b) by two bonds to the same carbon atom of ring A, in a geminal relationship (i.e., ring A and the heterocyclyl or $C_{3-6}$cycloalkyl attached thereto form a "spiro" bicyclic); or (c) by two bonds each connecting to adjacent carbon atoms of ring A in a vicinal relationship (i.e., ring A and the heterocyclyl or $C_{3-6}$cycloalkyl attached thereto are "fused").

In embodiments of formula I, formula IIA or formula IIB wherein $R^6$ is $C_{3-6}$cycloalkyl or heterocyclyl, such $C_{3-6}$cycloalkyl or heterocyclyl is joined to ring A by a single bond to an atom of ring A.

In embodiments of formula I, formula IIA or formula IIB wherein $R^6$ is $C_{3-6}$cycloalkyl or heterocyclyl, such $C_{3-6}$cycloalkyl or heterocyclyl is joined to ring A by two bonds to the same carbon atom of ring A, in a geminal relationship (i.e., ring A and the heterocyclyl or $C_{3-6}$cycloalkyl attached thereto form a "spiro" bicyclic.

In embodiments of formula I, formula IIA or formula IIB wherein $R^6$ is $C_{3-6}$cycloalkyl or heterocyclyl, such $C_{3-6}$cycloalkyl or heterocyclyl is joined to ring A by two bonds each connecting to adjacent carbon atoms of ring A in a vicinal relationship (i.e., ring A and the heterocyclyl or $C_{3-6}$cycloalkyl attached thereto are "fused").

In embodiments of formula I, formula IIA or formula IIB wherein $R^6$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl.

In embodiments of formula I, formula IIA or formula IIB wherein $R^6$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl.

In certain embodiments the invention provides compounds of the formula III:

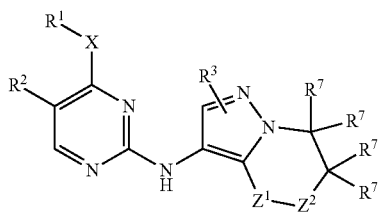

or a pharmaceutically acceptable salt thereof, wherein:
one of $Z^1$ and $Z^2$ is —O— or —$NR^7$— and the other is —$C(R^7)_2$—;
or both of $Z^1$ and $Z^2$ are —$C(R^7)_2$—;
each $R^7$ is independently: hydrogen; or $C_{1-6}$alkyl;
or two of $R^7$ together with the atom or atoms to which they are attached may form a four to seven membered unsaturated ring that is carbocyclic or which includes a heteroatom selected from O, N and S; and
$R^1$, $R^2$ and $R^3$ are as defined herein.

In certain embodiments of formula III, $Z^1$ is —O— and $Z^2$ is —$C(R^7)_2$.

In certain embodiments of formula III, $Z^1$ is —$NR^7$— and $Z^2$ is —$C(R^7)_2$.

In certain embodiments of formula III, $Z^2$ is —O— and $Z^1$ is —$C(R^7)_2$.

In certain embodiments of formula III, $Z^2$ is —$NR^7$— and $Z^1$ is —$C(R^7)_2$.

In certain embodiments of formula III, $Z^1$ and $Z^2$ are —$C(R^7)_2$.

In certain embodiments of formula III, at least one of $R^7$ is $C_{1-6}$alkyl.

In certain embodiments of formula III, one or two of $R^7$ are $C_{1-6}$alkyl.

In certain embodiments of formula III, one, two or three of $R^7$ are $C_{1-6}$alkyl.

In certain embodiments of formula III, two of $R^7$ together with the atom or atoms to which they are attached form a four to seven membered unsaturated ring that is carbocyclic or which includes a heteroatom selected from O, N and S.

In certain embodiments of formula III, two of $R^7$ together with the atom or atoms to which they are attached form a four to seven membered unsaturated carbocyclic ring.

In certain embodiments of formula III, two of $R^7$ together with the atom or atoms to which they are attached form a four to seven membered unsaturated ring that includes a heteroatom selected from O, N and S.

In embodiments of formula III wherein two of $R^7$ form a ring, such $R^7$ groups may be either: (a) bonded to the same carbon atom of ring A, in a geminal relationship (i.e., ring A and the ring formed by the $R^7$ groups attached thereto form a "spiro" bicyclic); (b) bonded to adjacent atoms of ring A in a vicinal relationship (i.e., ring A and the and the ring formed by the $R^7$ groups attached thereto are "fused"); or (c) bonded to separate non-adjacent atoms of ring A.

In embodiments of formula III wherein two of $R^7$ form a ring, such $R^7$ groups are bonded to the same carbon atom of ring A, in a geminal relationship (i.e., ring A and the ring formed by the $R^7$ groups attached thereto form a "spiro" bicyclic).

In embodiments of formula III wherein two of $R^7$ form a ring, such $R^7$ groups are bonded to adjacent atoms of ring A in a vicinal relationship (i.e., ring A and the and the ring formed by the $R^7$ groups attached thereto are "fused").

In embodiments of formula III wherein two of $R^7$ form a ring, such $R^7$ are bonded to separate non-adjacent atoms of ring A.

The invention also provides a method for treating a disease or condition mediated by or otherwise associated with the LRRK2 receptor, the method comprising administering to a subject in need thereof an effective amount of a compound of the invention.

The disease may be a neurodegenerative disease such as Parkinson's disease, Huntington's disease or Lewie body dementia.

The disease may be a CNS disorder such as Alzheimer's disease or L-Dopa induced dyskinesia.

The disease may be a cancer or proliferative disorder such as kidney, breast, prostate, blood, papillary or lung cancer, acute myelogenous leukemia, or multiple myeloma.

The disease may be an inflammatory disease such as leprosy, Crohn's disease, amyotrophic lateral sclerosis, rheumatoid arthritis, or ankylosing spondylytis.

The invention also provides a method for enhancing cognitive memory, the method comprising administering to a subject in need thereof an effective amount of a compound of the invention.

In embodiments the invention provides a compound as described herein for use as therapeutically active substance.

In embodiments the invention provides a compound as described herein for the use as therapeutically active substance for the therapeutic and/or prophylactic treatment of Parkinson's disease.

In embodiments the invention provides the use of a compound as described herein in the therapeutic and/or prophylactic treatment of Parkinson's disease.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I, wherein X, $R^1$, $R^2$, $R^3$, $R^4$ and $R^5$ are as defined herein.

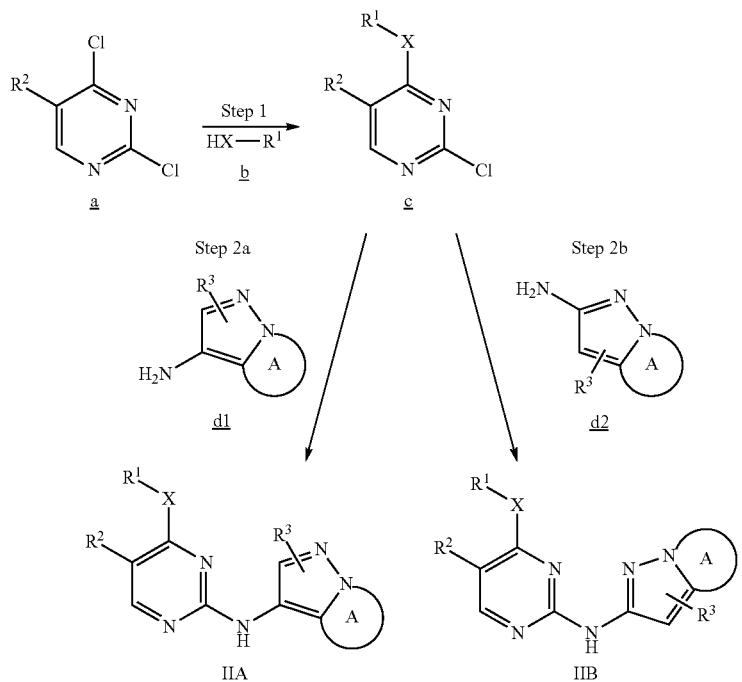

In step 1 of Scheme A, dichloropyrimidine compound a is reacted with reagent b to afford pyrimidine compound c. The reaction of step 1 may take place under polar solvent conditions. In embodiments of the invention where X is —O— (reagent b is an alcohol), the reaction of step 1 may be carried out in the presence of base.

Following step 1, one of steps 2a or 2b is carried out. In step 2a, pyrimidine compound c undergoes reaction with 4-amino-pyrazole compound d1 to provide an aminopyrimidine compound of formula IIa. In step 2b, pyrimidine compound c is reacted with 5-amino-pyrazole compound d2 to afford an aminopyrimidine compound of formula IIb. The reaction of steps 2a and 2b may take place in polar protic solvent and in the presence of acid such as HCl.

Many variations on the procedure of Scheme A are possible and will suggest themselves to those skilled in the art. Specific details for producing compounds of the invention are described in the Examples below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and in some embodiments 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of LRRK2-mediated diseases or conditions, including neurodegenerative diseases such as Parkinson's disease, Lewy body dementia and Huntington's disease, and for enhancement of cognitive memory generally in subjects in need thereof.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

ABBREVIATIONS

AcOH Acetic acid
AIBN 2,2'-Azobis(2-methylpropionitrile)
Atm. Atmosphere
$(BOC)_2O$ di-tert-Butyl dicarbonate
dba tris(dibenzylideneacetone)
DCM Dichloromethane/Methylene chloride
DIAD Diisopropyl azodicarboxylate
DIPEA Diisopropylethylamine
DMAP 4-Dimethylaminopyridine
DME 1,2-Dimethoxyethane
DMF N,N-Dimethylformamide
DMSO Dimethyl sulfoxide
DPPF 1,1'-Bis(diphenylphosphino)ferrocene
$Et_2O$ Diethyl ether
EtOH Ethanol/Ethyl alcohol
EtOAc Ethyl acetate
HATU 2-(1H-7-Azabenzotriazol-1-yl)-1,1,3,3-tetramethyl uronium hexafluorophosphate Methanaminium
HBTU O-Benzotriazol-1-yl-N,N,N',N'-tetramethyluronium hexafluorophosphate
HOBT 1-Hydroxybenzotriazole
HPLC High pressure liquid chromatography
RP HPLC Reverse phase high pressure liquid chromatography
i-PrOH Isopropanol/isopropyl alcohol
LCMS Liquid Chromatograph/Mass Spectroscopy
MeOH Methanol/Methyl alcohol
MW Microwaves
NBS N-Bromosuccinimide
NMP 1-Methyl-2-pyrrolidinone
PSI Pound per square inch
RT Room temperature
SFC Supercritical fluid chromatography
TBDMS tert-Butyldimethylsilyl
TFA Trifluoroacetic acid
THF Tetrahydrofuran
TLC Thin layer chromatography
Xphos 2-Dicyclohexylphosphino-2',4',6'-triisopropylbiphenyl Liquid Chromatography-Mass Spectrometry Method A LC-MS was performed on an Agilent 1200 Series LC coupled to an Agilent 6140 quadrupole mass spectrometer using an Agilent SD-C18 column (1.8 µm, 2.1×30 mm) with a linear gradient of 3-95% acetonitrile/water (with 0.05% trifluoroacetic acid in each mobile phase) within 8.5 minutes and held at 95% for 2.5 minutes.

Liquid Chromatography-Mass Spectrometry Method B

LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 um, 100×4.6 mm plus guard cartridge) with a linear gradient of 5-95% acetonitrile/water (with 0.1% formic acid in each mobile phase) within 3.5 minutes and held at 95% for 2.0 minutes.

Liquid Chromatography-Mass Spectrometry Method C

LC-MS was performed on a Waters 2795 Alliance HT HPLC with Waters 2996 Diode Array Detector coupled to a Micromass ZQ, single quadrapole mass spectrometer using a Waters Xterra MS C18 column (5 um, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.

Analytical Methods $^1H$ Nuclear magnetic resonance (NMR) spectroscopy was carried out using a Bruker instrument operating at 400 or 500 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad. Where thin layer chromatography (TLC) has been used it refers to silica gel TLC using silica gel MK6F 60 Å plates, $R_f$ is the distance traveled by the compound divided by the distance traveled by the solvent on a TLC plate. Flash chromatography refers to silica gel chromatography and is carried out using an SP4 or an Isolara 4 MPLC system (manufactured by Biotage); pre-packed silica gel cartridges (supplied by Biotage); or using conventional glass column chromatography.

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is an Initiator 60 supplied by Biotage. The actual power supplied varies during the course of the reaction in order to maintain a constant temperature.

Compounds made in the following examples are summarized in the Tables below, which shows affinity values for LRRK2 (Ki, micromolar) for representative compounds together with LCMS method (M), LC retention time (RT) in minutes, and Mass Spec m/z values (molecular weight).

Intermediate 1

2-Chloro-N-methyl-5-(trifluoromethyl)pyrimidin-4-amine

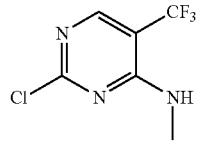

To a cooled (−10° C.) solution of 2,4-dichloro-5-trifluoromethylpyrimidine (20 g, 0.089 mol) in methanol (100 mL) was added triethylamine (12.5 mL, 0.089 mol) and a 2 M solution of methylamine in methanol (45 mL). The reaction was allowed to warm to room temperature and stirred overnight. The reaction was then concentrated and re-dissolved in ethyl acetate. The solution was washed with sat. NaHCO$_3$, brine, dried over MgSO$_4$, filtered and concentrated. The crude product was purified by column chromatography (5-25% EtOAc in heptane) to give 2-chloro-N-methyl-5-(trifluoromethyl)pyrimidin-4-amine (8.6 g, 45%). $^1$H-NMR (DMSO): δ 8.37 (s, 1H), 7.90 (s, 1H), 2.90 (s, 3H).

Additional intermediates prepared using similar methods as described above are listed in Table 1 below:

TABLE 1

| 2 | 2-chloro-N-ethyl-5-(trifluoromethyl)pyrimidin-4-amine | 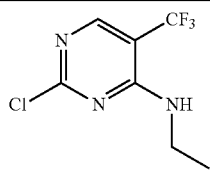 |
|---|---|---|
| 3 | 2-chloro-N-cyclopropyl-5-(trifluoromethyl)pyrimidin-4-amine | 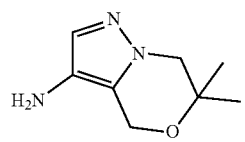 |
| 4 | 2-chloro-4-(methylamino)pyrimidine-5-carbonitrile | |

TABLE 1-continued

Intermediate 5

6,6-dimethyl-6,7-dihydro-4H-pyrazolo[5,1-c][1,4]oxazin-3-amine

Step 1—1-(benzyloxy)-2-methylpropan-2-ol

To a solution of 2,2-dimethyloxirane (15.0 mL, 168 mmol) and phenylmethanol (4.8 mL) in toluene (40 mL) was added 50% a.q. NaOH (12 mL). The mixture was stirred at 100° C. for 30 h. Water was added and the mixture was extracted with ethyl acetate. The organic layer was combined, washed with brine, dried over with Na$_2$SO$_4$, and concentrated. The residue was purified by silica gel column chromatography eluting with petroleum ether/ethyl acetate (5/1) to afford the title compound (9.36 g, 99%) as yellow oil. $^1$H NMR (500 MHz, CDCl$_3$) δ 7.30-7.38 (m, 5H), 4.58 (s, 2H), 3.31 (s, 2H), 2.05 (s, 1H), 1.23 (s, 6H).

Step 2—((2-methyl-2-(prop-2-ynyloxy)propoxy)methyl)benzene

To a mixture of NaH (5.0 g) in THF (50 mL) at 0° C. was added 1-(benzyloxy)-2-methylpropan-2-ol (9.36 g, 51.9 mmol) dropwise. After being stirred at room temperature for 0.5 h, 3-bromoprop-1-yne (12.4 g, 104 mmol) was added slowly at 0° C. The mixture was then stirred at reflux overnight. The reaction was quenched by addition of sat. NH$_4$Cl. The resulting mixture was extracted with ethyl acetate (30 mL×3). The organic layer was combined, dried over with Na$_2$SO$_4$, and concentrated. The residue was purified by silica gel column chromatography eluting with petroleum ether/ethyl acetate (20/1) to afford the title compound (9.72 g, 86%) as pale yellow oil. $^1$H NMR (500 MHz, CDCl$_3$) δ 7.34-7.35 (m, 5H), 4.56 (s, 2H), 4.18 (d, J=2.0 Hz, 2H), 3.38 (s, 2H), 2.34 (t, J=2.0 Hz, 1H), 1.25 (s, 6H).

Step 3—3-((1-(benzyloxy)-2-methylpropan-2-yloxy)methyl)-1H-pyrazole

A mixture of ((2-methyl-2-(prop-2-ynyloxy)propoxy)methyl)benzene (1.00 g, 4.58 mmol) and (diazomethyl)trimethylsilane (2.29 mL) was stirred at 135° C. under microwave irradiation for 1 h. Removal of the solvent afforded the title compound (1.19 g, 80%). LC-MS (ESI): m/z=261.2 (M+H)⁺.

Step 4—2-((1H-pyrazol-3-yl)methoxy)-2-methylpropan-1-ol

A mixture of 3-((1-(benzyloxy)-2-methylpropan-2-yloxy)methyl)-1H-pyrazole (5.5 g, 21 mmol) and 10% Pd(OH)$_2$/C (2.2 g) in EtOH (100 mL) was stirred at 100° C. under H$_2$ (4 atm) for 12 h. The insoluble material was filtered off and the filtrate was concentrated to afford the title compound (3.0 g, 83%). LC-MS (ESI): m/z=171.1 (M+H)⁺.

Step 5—2-((4-bromo-1H-pyrazol-3-yl)methoxy)-2-methylpropan-1-ol

To a solution of 2-((1H-pyrazol-3-yl)methoxy)-2-methylpropan-1-ol (3.00 g, 17.6 mmol) in acetonitrile (30 mL) was added NBS (3.45 g, 19.4 mmol) in one portion. After being stirred overnight, the mixture was concentrated. The residue was purified by reverse phase Combiflash to give the title compound (1.8 g, 41%). LC-MS (ESI): m/z=249.1 (M+H)⁺.

Step 6—2-methyl-2-((4-nitro-1H-pyrazol-5-yl)methoxy)propyl nitrate

To a cooling (0° C.) flask with 2-((4-bromo-1H-pyrazol-3-yl)methoxy)-2-methylpropan-1-ol (300 mg, 1.2 mmol) was added fuming nitric acid (3.0 mL). After being stirred for 1 h at 0° C. and the reaction was quenched with ice. The mixture was extracted with ethyl acetate (25 mL×3). The organic layers were washed with water and brine, dried over sodium sulfate, and concentrated in vacuo to give the title compound (260 mg, 52%, 69% purity). LC-MS (ESI): m/z=261.2 (M+H)⁺.

Step 7—6,6-dimethyl-3-nitro-6,7-dihydro-4H-pyrazolo[5,1-c][1,4]oxazine

To a cooling (0° C.) solution of 2-methyl-2-((4-nitro-1H-pyrazol-5-yl)methoxy)-propyl nitrate (580 mg, 1.12 mmol) in DMF (15 mL) was added NaH (89.0 mg, 2.23 mmol). The mixture was stirred overnight. This reaction was quenched by ice and the mixture was extracted with ethyl acetate (30 mL×3). The organic layers were washed with water and brine, dried over Na$_2$SO$_4$, and concentrated in vacuo. The residue was purified by silica gel column chromatography eluting with petroleum ether/ethyl acetate (20/1 to 5/1) to give the title compound (43.5 mg, 20%). LC-MS (ESI): m/z=198.3 (M+H)⁺.

Step 8—6,6-dimethyl-6,7-dihydro-4H-pyrazolo[5,1-c][1,4]oxazin-3-amine

To a cooling (0° C.) solution of 6,6-dimethyl-3-nitro-6,7-dihydro-4H-pyrazolo[5,1-c][1,4]oxazine (35.0 mg, 0.177 mmol) in THF/MeOH (3 mL/3 mL) was added Raney Ni (100 mg) and hydrazine hydrate (1 mL). After being stirred for 16 h, the insoluble material was filtered off. The filtrate was concentrated in vacuo to give the title compound (26 mg, 89%). LC-MS (ESI): m/z=168.1 (M+H)⁺.

Intermediate 6

4,5-dimethyl-4,5,6,7-tetrahydropyrazolo[1,5-a]pyrazin-3-amine

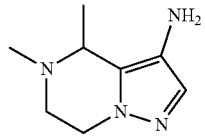

Step 1—4-nitro-1-(tetrahydro-2H-pyran-2-yl)-1H-pyrazole

To a solution of 4-nitro-1H-pyrazole (5650 mg, 50.00 mmol) and PTSA (860 mg, 5.00 mmol) in DCM (50 mL) at 0° C. was added a solution of DHP (5040 mg, 60.00 mmol) in DCM (10 mL) dropwise. After being stirred at room temperature for 20 h, the mixture was concentrated. The residue was purified by silica gel column chromatography eluting with petroleum ether/ethyl acetate (5/1) to afford the title compound (8.5 g, 86%). LC-MS (ESI): m/z=198 (M+H)⁺.

Step 2—5-chloro-4-nitro-1-(tetrahydro-2H-pyran-2-yl)-1H-pyrazole

To a solution of 4-nitro-1-(tetrahydro-2H-pyran-2-yl)-1H-pyrazole (7880 mg, 40.00 mmol) in THF (100 mL) at −70° C. was added LHMDS (1 N in THF, 44 mL) under N$_2$ over 40 min. After being stirred at −30° C. for 30 min, the mixture was cooled −70° C. again. A solution of C$_2$Cl$_6$ (10.5 g, 44.0 mmol) in THF (60 mL) was added at this temperature. The mixture was allowed to warm to room temperature and stirred for 2 h. The reaction was quenched with H$_2$O (2 mL). After concentration, the residue was purified by silica gel column chromatography eluting with petroleum ether/ethyl acetate (8/1) to afford the title compound (7.5 g, 81%) as a yellow solid. LC-MS (ESI): m/z=232 (M+H)⁺.

Step 3—5-(1-ethoxyvinyl)-4-nitro-1-(tetrahydro-2H-pyran-2-yl)-1H-pyrazole

A mixture of 5-chloro-4-nitro-1-(tetrahydro-2H-pyran-2-yl)-1H-pyrazole (6.93 g, 30.0 mmol), tributyl-(1-ethoxyvinyl)stannane (11.9 g, 33.0 mmol), and Pd(PPh$_3$)$_4$ (1.74 g, 1.50 mmol) in dioxane (100 mL) was refluxed under N$_2$ for 20 h. After cooling down, KF (1.0 g) was added. The insoluble material was filtered off and the filtrate was concentrated. The residue was purified by silica gel column chromatography eluting with petroleum ether/ethyl acetate (10/1) to afford the title compound (6.5 g, 80%) as a white solid. LC-MS (ESI): m/z=268 (M+H)⁺.

Step 4—1-(4-nitro-1-(tetrahydro-2H-pyran-2-yl)-1H-pyrazol-5-yl)ethanone

To a solution of 5-(1-ethoxyvinyl)-4-nitro-1-(tetrahydro-2H-pyran-2-yl)-1H-pyrazole (2.67 g, 10.0 mmol) in methanol (20 mL) was added 2 N HCl/methanol (10 mL). The mixture was stirred for 10 h. After concentration, the residue was purified by silica gel column chromatography eluting with petroleum ether/ethyl acetate (5/1) to afford the title compound (1.5 g, 63%) as oil. LC-MS (ESI): m/z=240 (M+H)⁺.

Step 5—2-(methyl(1-(4-nitro-1-(tetrahydro-2H-pyran-2-yl)-1H-pyrazol-5-yl)ethyl)amino)ethanol A mixture of 1-(4-nitro-1-(tetrahydro-2H-pyran-2-yl)-1H-pyrazol-5-yl)ethanone (1.2 g, 5.0 mmol), 2-(methylamino) ethanol (450 mg, 6.00 mmol), NaBH$_3$CN (630 mg, 10.0 mmol), and ZnCl$_2$ (68 mg, 0.50 mmol) in methanol (20 mL) was refluxed for 2 h. After cooling down, the mixture was concentrated. The residue was purified by reverse phase Combiflash to afford the title compound (820 mg, 88%) as a yellow solid. LC-MS (ESI): m/z=299 (M+H)$^+$.

Step 6—2-(methyl(1-(4-nitro-1H-pyrazol-5-yl)ethyl)amino)ethanol

A solution of 2-(methyl(1-(4-nitro-1-(tetrahydro-2H-pyran-2-yl)-1H-pyrazol-5-yl)ethyl)amino)ethanol (750 mg, 2.50 mmol) and SOBr$_2$ (1.04 g, 5.00 mmol) in toluene (10 mL) was stirred at room temperature for 2 h. After concentration, the residue was purified by reverse phase Combiflash to afford the title compound (460 mg, 85%) as a white solid. LC-MS (ESI): m/z=215 (M+H)$^+$.

Step 7—4,5-dimethyl-3-nitro-4,5,6,7-tetrahydropyrazolo[1,5-a]pyrazine

To a solution of 2-(methyl(1-(4-nitro-1H-pyrazol-5-yl)ethyl)amino)ethanol (430 mg, 2.00 mmol) and PPh$_3$ (786 mg, 3.00 mmol) in THF (10 mL) at 0° C. was added DIAD (606 mg, 3.00 mmol). After being stirred at 50° C. for 2 h, the mixture was concentrated. The residue was purified by reverse phase Combiflash to afford the title compound (260 mg, 66%) as a white solid. LC-MS (ESI): m/z=197 (M+H)$^+$.

Step 8—4,5-dimethyl-4,5,6,7-tetrahydropyrazolo[1,5-a]pyrazin-3-amine

To a solution of 4,5-dimethyl-3-nitro-4,5,6,7-tetrahydropyrazolo[1,5-a]pyrazine (260 mg, 1.30 mmol) in methanol (5 mL) was added Raney Ni (50 mg) and hydrazine hydrate (2 mL). The mixture was stirred at room temperature for 2 h. The insoluble was filtered off and the filtrate was concentrated to afford the title compound (200 mg, 91%) as a white solid. LC-MS (ESI): m/z=167 (M+H)$^+$.

Intermediate 7

(6R)-4,6-dimethyl-6,7-dihydro-4H-pyrazolo[5,1-c][1,4]oxazin-3-amine

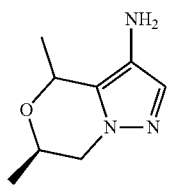

Step 1—(((2R)-2-(but-3-yn-2-yloxy)propoxy)methyl)benzene

To a suspension of sodium hydride (60 wt % dispersion in mineral oil) (1380 mg, 34.6 mmol) in tetrahydrofuran (100 mL) cooled to 0° C. was added (2R)-1-benzyloxypropan-2-ol (5.00 g, 30.1 mmol) dropwise. The solution was stirred at 0° C. for 1 h then 1-methylprop-2-ynyl methanesulfonate (4780 mg, 32.3 mmol) was added dropwise and the reaction mixture was allowed to warm to room temp and stirred overnight. The reaction mixture was quenched by the addition of sat. aq. ammonium chloride and extracted with EtOAc. The combined organics were washed with brine, dried over sodium sulfate, filtered and concentrated in vacuo. The crude residue was adsorbed onto silica and purified by column chromatography (0-20% EtOAc in Heptane) to afford the title compound as a yellow oil (2.36 g, 36%, mixture of diastereomers).

Step 2—5-(1-(((R)-1-(benzyloxy)propan-2-yl)oxy)ethyl)-1H-pyrazole

To a microwave vial containing [(2R)-2-(1-methylprop-2-ynyloxy)propoxy]methylbenzene (1000 mg, 4.58 mmol) was added (trimethylsilyl)diazomethane (2.0 mol/L in hexanes) (2.9 mL, 5.73 mmol). The vial was capped and heated to 135° C. in the microwave for 40 mins. The reaction mixture was concentrated in vacuo, adsorbed onto silica and purified by flash column chromatography (0-100% EtOAc in heptane) to afford the title compound as a yellow oil (1.04 g, 87%, mixture of diastereomers). LC-MS (ESI): m/z=261.2 (M+H)$^+$.

Step 3—(2R)-2-(1-(1H-pyrazol-5-yl)ethoxy)propan-1-ol

To a round-bottomed flask equipped with a reflux condenser containing 5-[1-[(1R)-2-benzyloxy-1-methyl-ethoxy]ethyl]-1H-pyrazole (1040 mg, 4.00 mmol) was added ethanol (35 mL) then palladium hydroxide on carbon (20 wt %) (281 mg, 0.40 mmol). Nitrogen was first bubbled through the solution, followed by bubbling hydrogen for 5 mins each. The solution was then heated to reflux (80° C.) overnight. The reaction mixture was cooled to room temp and filtered through celite, eluting with dichloromethane. The filtrate was concentrated in vacuo to afford the title compound (674 mg, 99%, mixture of diastereomers). LC-MS (ESI): m/z=171.1 (M+H)$^+$.

Step 4—(2R)-2-(1-(4-nitro-1H-pyrazol-5-yl)ethoxy)propyl nitrate

To a solution of (2R)-2-[1-(1H-pyrazol-5-yl)ethoxy]propan-1-ol (674 mg, 3.96 mmol) in sulfuric acid 15.0 mL, 276 mmol) cooled to 0° C. was added fuming nitric acid (15.0 mL) dropwise. The reaction mixture was stirred at 0° C. and allowed to warm slowly to room temp overnight. Quenched by pouring into 100 mL of ice water and slowly added solid sodium carbonate portionwise (Caution: Vigourous reaction!) until all acid was quenched. The reaction mixture was poured into a separatory funnel and extracted with EtOAc. The combined organics were washed with brine, dried over sodium sulfate, filtered and concentrated in vacuo to afford the title compound as a dark orange oil (952 mg, 92%, mixture of diastereomers).

Step 5—(6R)-4,6-dimethyl-3-nitro-6,7-dihydro-4H-pyrazolo[5,1-c][1,4]oxazine

To a solution of [(2R)-2-[1-(4-nitro-1H-pyrazol-5-yl)ethoxy]propyl]nitrate (952 mg, 3.66 mmol) in N,N-dimethylformamide (30 mL, 387 mmol) cooled to 0° C. was added 60% sodium hydride in oil (176 mg, 4.39 mmol. The reaction mixture was allowed to slowly warm to room temp and stirred overnight. The reaction mixture was quenched by pouring into ice-cold water and extracted with EtOAc. The combined organics were washed with brine, dried over sodium sulfate, filtered and concentrated in vacuo. The residue was adsorbed onto silica and purified by column chromatography (0-100% EtOAc in heptane) to afford the title compound (408 mg, 57%, mixture of diastereomers). LC-MS (ESI): m/z=198.0 (M+H)+.

Step 6—(6R)-4,6-dimethyl-6,7-dihydro-4H-pyrazolo[5,1-c][1,4]oxazin-3-amine

To a round-bottomed flask was added (6R)-4,6-dimethyl-3-nitro-6,7-dihydro-4H-pyrazolo[5,1-c][1,4]oxazine (408 mg, 2.07 mmol). The flask was purged with nitrogen and ethanol (35 mL, 575 mmol) was added followed by 10% palladium on carbon (220 mg, 0.21 mmol). A hydrogen balloon was added and hydrogen was bubbled through the reaction mixture for 5 mins. The reaction mixture was stirred overnight at room temp then diluted with dichloromethane, filtered through celite, eluting with dichloromethane and concentrated in vacuo to afford the title compound (344 mg, 99%, mixture of diastereomers). LC-MS (ESI): m/z=168.1 (M+H)+.

Intermediate 8

(6S)-4,6-dimethyl-6,7-dihydro-4H-pyrazolo[5,1-c][1,4]oxazin-3-amine

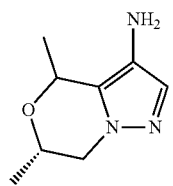

(6S)-4,6-Dimethyl-6,7-dihydro-4H-pyrazolo[5,1-c][1,4]oxazin-3-amine was prepared in a manner analogous to that of (6R)-4,6-dimethyl-6,7-dihydro-4H-pyrazolo[5,1-c][1,4]oxazin-3-amine, starting from (2S)-1-benzyloxypropan-2-ol.

Intermediate 9

5,6-dihydro-4H-pyrrolo[1,2-b]pyrazol-3-amine

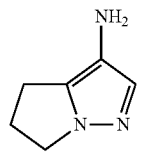

Step 1—5,6-dihydro-4H-pyrrolo[1,2-c][1,2,3]oxadiazol-7-ium-3-olate

To a solution of L-Proline (1000 mg, 8.69 mmol) and sodium nitrite (845 mg, 12.2 mmol) in water 2.00 mL) cooled to 0° C. was slowly added concentrated hydrochloric acid (1.0 mL, 11.6 mmol). The reaction mixture was allowed to warm to room temp and stirred overnight. The reaction mixture was diluted with water and extracted with MTBE, dried over sodium sulfate and concentrated in vacuo. The crude residue was then taken up in toluene (4.00 mL) and cooled to 0° C. Trifluoroacetic anhydride (1.81 mL, 13.0 mmol) was then added and the reaction was stirred overnight at room temp. The reaction mixture was concentrated in vacuo, adsorbed onto silica and purified by column chromatography (0-10% MeOH in DCM) to afford the title compound as a brown oil (0.807 g, 74%)¹H NMR (400 MHz, CDCl3) δ 4.43 (t, J=7.6 Hz, 2H), 2.96-2.86 (m, 2H), 2.85-2.73 (m, 2H). LC-MS (ESI): m/z=127.0 (M+H)+.

Step 2—ethyl 5,6-dihydro-4H-pyrrolo[1,2-b]pyrazole-3-carboxylate

A mixture of 5,6-dihydro-4H-pyrrolo[1,2-c]oxadiazol-7-ium-3-olate (355.4 mg, 2.82 mmol) and ethyl propiolate (0.87 mL, 8.46 mmol) in xylene (10 mL) in a round-bottom flask equipped with a condenser was heated to 125° C. overnight. The reaction mixture was concentrated in vacuo, adsorbed onto silica and purified by column chromatography (0-100% EtOAc in Heptane) to afford the title compound as a yellow oil (161 mg, 32%, more polar regioisomer). ¹H NMR (400 MHz, CDCl3) δ 7.90 (s, 1H), 4.27 (q, J=7.1 Hz, 2H), 4.16 (t, J=7.3 Hz, 2H), 3.09 (t, J=7.4 Hz, 2H), 2.70-2.60 (m, 2H), 1.33 (t, J=7.1 Hz, 3H). LC-MS (ESI): m/z=181.1 (M+H)+.

Step 3—5,6-dihydro-4H-pyrrolo[1,2-b]pyrazole-3-carboxylic acid

To a vial containing ethyl 5,6-dihydro-4H-pyrrolo[1,2-b]pyrazole-3-carboxylate (171 mg, 0.95 mmol) was added water (5 mL) followed by potassium hydroxide (266.20 mg, 4.74 mmol). The vial was capped with a teflon-lined cap and heated to 80° C. for 3 h. The product was acidified with concentrated HCl and concentrated in vacuo. The crude residue was taken up in EtOAc and filtered. The filtrate was concentrated in vacuo to afford the title compound as a white solid (89 mg, 62%). ¹H NMR (400 MHz, CDCl3) δ 7.18 (s, 1H), 4.05 (t, J=7.2 Hz, 2H), 2.84-2.75 (m, 2H), 2.70 (s, 2H), 2.63-2.49 (m, 2H). ¹H NMR (400 MHz, DMSO) δ 12.06 (s, 1H), 7.75 (s, 1H), 4.12-4.06 (m, 2H), 3.00-2.92 (m, 2H), 2.61-2.52 (m, 2H). LC-MS (ESI): m/z=153.0 (M+H)+.

Step 4—benzyl (5,6-dihydro-4H-pyrrolo[1,2-b]pyrazol-3-yl)carbamate

To a solution of 5,6-dihydro-4H-pyrrolo[1,2-b]pyrazole-3-carboxylic acid (24.2 mg, 0.159 mmol) in dioxane (2.0 mL) and benzyl alcohol (0.0333 mL, 0.318 mmol) was added N,N-diisopropylethylamine (0.0834 mL, 0.477 mmol) and diphenylphosphoryl azide (0.0354 mL, 0.159 mmol). The mixture was then heated to 110° C. for 2 hours. The reaction mixture was concentrated in vacuo and purified by reverse-phase HPLC to afford the title compound with an unidentified byproduct. This material was used directly in the next step.

Step 5—5,6-dihydro-4H-pyrrolo[1,2-b]pyrazol-3-amine

To a solution of benzyl N-(5,6-dihydro-4H-pyrrolo[1,2-b]pyrazol-3-yl)carbamate (42.8 mg, 0.166 mmol) in ethanol (5 mL, 82.2 mmol) was added palladium on activated carbon (10 wt %) (17.7 mg, 0.0166 mmol). Nitrogen was bubbled through the mixture for 5 mins then hydrogen was bubbled through the solution for 5 mins. The reaction was stirred under an atmosphere of hydrogen for 2 h. The reaction mixture was filtered through celite, eluting with DCM, concentrated in vacuo. The residue was adsorbed onto silica and purified by flash column chromatography (0-10% MeOH in DCM) to afford the title compound (7.8 mg, 39% over two steps). $^1$H NMR (400 MHz, CDCl3) δ 7.18 (s, 1H), 4.05 (t, J=7.2 Hz, 2H), 2.84-2.75 (m, 2H), 2.70 (s, 2H), 2.63-2.49 (m, 2H).

Intermediate 10

5-methyl-4,5,6,7-tetrahydropyrazolo[1,5-a]pyrazin-3-amine

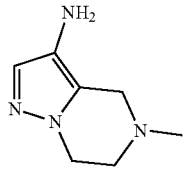

Step 1—2-(methyl((4-nitro-1H-pyrazol-5-yl)methyl)amino)ethanol

To a solution of (4-nitro-1H-pyrazol-5-yl)methanol (550 mg, 3.85 mmol) and carbon tetrabromide (1.40 g, 4.23 mmol) in dry DCM (30 mL) at 0° C. was added a solution of triphenylphosphine (1.12 g, 4.23 mmol) in DCM (10 mL), dropwise over a period of 20 min. After stirring the mixture at 0° C. for 1 h, N-methylethanolamine (0.34 mL, 4.23 mmol) was added followed by DIPEA (0.85 mL, 4.81 mmol). After stirring in a cold water bath (−10° C.) for 1 h, the mixture was concentrated. The residue was purified by silica gel column chromatography, eluting with DCM/10% MeOH/NH$_3$ (100/0 to 0/100), to give the title product as amber oil (0.79 g, 100%). $^1$H NMR (400 MHz, CDCl$_3$) δ 8.14 (s, 1H), 4.11 (s, 2H), 3.80 (t, J=4.8 Hz, 2H), 3.49 (s, 1H), 2.70 (t, J=4.8 Hz, 2H), 2.46 (s, 3H). LC-MS (ESCI): m/z=201 (M+H)$^+$.

Step 2—5-methyl-3-nitro-4,5,6,7-tetrahydropyrazolo[1,5-a]pyrazine

To a solution of 2-(methyl((4-nitro-1H-pyrazol-5-yl)methyl)amino)ethanol (0.79 g, 3.95 mmol) and triphenylphosphine (3.1 g, 11.85 mmol) in dry THF (25 mL) at 0° C. was added diethyl azodicarboxylate (1.86 mL, 11.85 mmol) dropwise over 5 min. The mixture was allowed to stir and warm to room temp over 72 h. The mixture was diluted with ethyl acetate (50 mL) and water (30 mL). The layers were separated and the aqueous phase was washed with ethyl acetate (2×30 mL). Aqueous 2 M HCl was added and the layers were separated. The aqueous phase was basified with aqueous 2 M sodium hydroxide and extracted with DCM. The organic phase was passed through a hydrophobic frit and the solvent was removed in vacuo. The residue was purified on SCX cartridge eluting with methanol then with 7N NH$_3$/MeOH to give the title compound as an off-white solid (122 mg, 17%). $^1$H NMR (400 MHz, CDCl$_3$) δ 8.08 (s, 1H), 4.24 (t, J=5.5 Hz, 2H), 4.01 (s, 2H), 2.94 (t, J=5.5 Hz, 2H), 2.57 (s, 3H). LC-MS: m/z=183 (M+H)$^+$.

Step 3—5-methyl-4,5,6,7-tetrahydropyrazolo[1,5-a]pyrazin-3-amine

To a solution of 5-methyl-3-nitro-4,5,6,7-tetrahydropyrazolo[1,5-a]pyrazine (122 mg, 0.67 mmol) in ethanol (10 mL) was added palladium on carbon (25 mg, 10 wt %). The mixture was degassed with nitrogen and shaken under a hydrogen atmosphere (40 psi) for 3 h. The mixture was filtered through a celite cartridge and the filtrate concentrated to give the title compound as a dark green gum (120 mg, quant.). $^1$H NMR (400 MHz, CDCl$_3$) δ 7.16 (s, 1H), 4.13 (t, J=5.7 Hz, 2H), 3.56 (s, 2H), 3.48 (s, 2H), 2.86 (t, J=5.7 Hz, 2H), 2.52 (s, 3H): LC-MS (ESCI): m/z=153 (M+H)$^+$.

Intermediate 11

1-(2-(tert-butyldimethylsilyloxy)ethyl)-4-nitro-1H-pyrazole

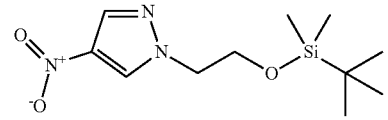

To a mixture of 4-nitropyrazole (904 mg, 8 mmol) and potassium carbonate (3.3 g, 24 mmol) in DMF (10 mL) was added (2-bromoethoxy)(tert-butyl)dimethylsilane (0.6 mL, 2.9 mmol) and the mixture was heated to 50° C. for 2 h. Further (2-bromoethoxy)(tert-butyl)dimethylsilane (1.4 mL, 6.7 mmol) was added and the mixture was heated to 50° C. for 4 h. The solvent was removed in vacuo and the residue was partitioned between DCM (10 mL) and water (10 mL). The organic phase was passed through a hydrophobic frit and the solvent was removed in vacuo. The residue was purified by silica gel column chromatography, eluting with iso-hexane/ethyl acetate (100/0 to 0/100), to give the title compound (2.15 g, 99%) as a white solid. $^1$H NMR (400 MHz, CDCl$_3$) δ 8.20 (s, 1H), 8.08 (s, 1H), 4.24 (t, J=4.9 Hz, 2H), 3.95 (t, J=4.9 Hz, 2H), 0.84 (s, 9H), −0.04 (s, 6H). LC-MS (ESCI): m/z=272 (M+H)$^+$.

Intermediate 12

6',7'-dihydrospiro[oxetane-3,4'-pyrazolo[5,1-c][1,4]oxazin]-3'-amine

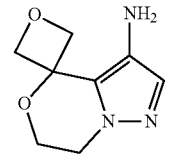 [SMILES: Nc1cnn2c1C1(COC1)OCC2]

Step 1—3-(1-(2-(tert-butyldimethylsilyloxy)ethyl)-4-nitro-1H-pyrazol-5-yl)oxetan-3-ol To a solution of 1-(2-(tert-butyldimethylsilyloxy)ethyl)-4-nitro-1H-pyrazole (542 mg, 2 mmol) in THF (2 mL) at −78° C. was added lithium bis(trimethylsilyl)amide (8 mL, 1 M, in THF, 8 mmol) dropwise over 10 min. The mixture was allowed to stir at −78° C. for 25 min and then slowly allowed to warm to −45° C. The mixture was then recooled to −78° C. and oxetan-3-one (187 mg, 2.6 mmol) in THF (2.5 mL) added dropwise. The mixture was allowed to stir at −78° C. for 1 h and then quenched by the addition of saturated aqueous ammonium chloride solution (10 mL). The mixture was allowed to warm to room temperature and then DCM (20 mL) was added. The organic phase was passed through a hydrophobic frit and the solvent was removed in vacuo. The residue was purified by silica gel column chromatography, eluting with iso-hexane/ethyl acetate (100/0 to 0/100), to give the title compound (338 mg, 49%) as an off-white solid. $^1$H NMR (400 MHz, CDCl$_3$) δ 8.16 (s, 1H), 5.18-5.15 (m, 2H), 4.93-4.90 (m, 2H), 4.35 (s, 1H), 4.03 (s, 4H), 0.83 (s, 9H), 0.04 (s, 6H). LC-MS (ESCI): m/z=344 (M+H)$^+$.

Step 2—3-(1-(2-hydroxyethyl)-4-nitro-1H-pyrazol-5-yl)oxetan-3-ol

To a solution of 3-(1-(2-(tert-butyldimethylsilyloxy)ethyl)-4-nitro-1H-pyrazol-5-yl)oxetan-3-ol (338 mg, 0.98 mmol) in THF (6 mL) was added tetrabutylammonium fluoride (3 mL, 1 M in THF, 3 mmol). The mixture was allowed to stir at room temperature for 3 h. Saturated aqueous sodium bicarbonate solution (10 mL) and DCM (10 mL) were added and the organic phase was passed through a hydrophobic frit. The residue was purified by silica gel column chromatography, eluting with iso-hexane/ethyl acetate/10% MeOH in DCM (100/0/0 to 0/100/0 to 0/0/100), to give the title compound (171 mg, 76%) as an off-white solid. $^1$H NMR (400 MHz, CDCl$_3$) δ 8.14 (s, 1H), 5.14-5.11 (m, 2H), 4.92-4.89 (m, 2H), 4.11-4.03 (m, 4H), 3.49 (s, 1H). LC-MS (ESCI): m/z=230 (M+H)$^+$.

Step 3—3'-nitro-6',7'-dihydrospiro[oxetane-3,4'-pyrazolo[5,1-c][1,4]oxazine]

To a solution of 3-(1-(2-hydroxyethyl)-4-nitro-1H-pyrazol-5-yl)oxetan-3-ol (160 mg, 0.7 mmol) in DCM (7 mL) was added DMAP (1 mg, 0.01 mmol), followed by a solution of tosyl chloride (153 mg, 0.8 mmol) in DCM (1 mL). The mixture was cooled to 0° C. and then triethylamine (0.44 mL, 3.5 mmol) added. The mixture was stirred at room temperature for 3 h and then water (10 mL) was added. The organic phase was passed through a hydrophobic frit and the solvent was removed in vacuo. The residue was dissolved in THF (5 mL) and sodium hydride (28 mg, 60% in oil, 0.7 mmol) was added. The mixture was stirred at room temperature for 8 h. Water (50 mL) and DCM (50 mL) were added and the organic phase was passed through a hydrophobic frit. The solvent was removed in vacuo and the residue was purified by silica gel column chromatography, eluting with iso-hexane/ethyl acetate (100/0 to 0/100), to give the title compound (86 mg, 58%) as an off-white solid. $^1$H NMR (400 MHz, CDCl$_3$) δ 8.18 (s, 1H), 5.31 (d, J=7.1 Hz, 2H), 4.73 (d, J=7.1 Hz, 2H), 4.25 (app dd, J=5.5, 4.7 Hz, 2H), 4.14 (app dd, J=5.5, 4.7 Hz, 2H). LC-MS (ESCI): m/z=212 (M+H)$^+$.

Step 4—6',7'-dihydrospiro[oxetane-3,4'-pyrazolo[5,1-c][1,4]oxazin]-3'-amine

To a solution of 3'-nitro-6',7'-dihydrospiro[oxetane-3,4'-pyrazolo[5,1-c][1,4]oxazine] (86 mg, 0.41 mmol) in a mixture of ethanol (10 mL) and ethyl acetate (5 mL) was added palladium on carbon (25 mg, 10 wt %). The mixture was degassed with nitrogen and shaken under a hydrogen atmosphere (30 psi) for 6 h. The mixture was filtered through celite and the celite washed with ethanol. The solvent was removed in vacuo to give the title compound (73 mg, 98%) as a yellow oil. $^1$H NMR (400 MHz, CDCl$_3$) δ 7.20 (s, 1H), 4.98-4.91 (m, 4H), 4.10-4.06 (m, 2H), 4.01-3.97 (m, 2H), 3.33 (br s, 2H). LC-MS (ESCI): m/z=182 (M+H)$^+$.

Intermediate 13

4,4-dimethyl-6,7-dihydro-4H-pyrazolo[5,1-c][1,4]oxazin-3-amine

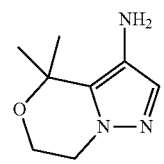

Step 1—2-(1-(2-(tert-butyldimethylsilyloxy)ethyl)-4-nitro-1H-pyrazol-5-yl)propan-2-ol To a solution of 1-(2-(tert-butyldimethylsilyloxy)ethyl)-4-nitro-1H-pyrazole (1 g, 3.68 mmol) in THF (4 mL) at −78° C. was added lithium bis(trimethylsilyl)amide (14.7 mL, 1 M, in THF, 14.7 mmol) dropwise over 10 min. The mixture was allowed to stir at −78° C. for 25 min and then slowly allowed to warm to −45° C. The mixture was then recooled to −78° C. and acetone (0.35 mL, 4.8 mmol) in THF (5 mL) added dropwise. The mixture was allowed to stir at −78° C. for 1 h and then quenched by the addition of saturated aqueous ammonium chloride solution (10 mL). The mixture was allowed to warm to room temperature and then DCM (20 mL) was added. The organic phase was passed through a hydrophobic frit and the solvent was removed in vacuo. The residue was purified by silica gel column chromatography, eluting with iso-hexane/ethyl acetate (100/0 to 0/100) and then again eluting with iso-hexane/diethyl ether (100/0 to 0/100), to give the title compound (LC-MS (ESCI): m/z=330 (M+H)$^+$) as a mixture with 1-(2-(tert-butyldimethylsilyloxy)ethyl)-4-nitro-1H-pyrazole.

Step 2—2-(1-(2-hydroxyethyl)-4-nitro-1H-pyrazol-5-yl)propan-2-ol

The product mixture from step 1 was dissolved in THF (20 mL) and tetrabutylammonium fluoride (10 mL, 1 M in THF, 10 mmol) was added. The mixture was allowed to stir at room temperature for 3 h. Saturated aqueous sodium bicarbonate solution (10 mL) and DCM (10 mL) were added and the organic phase was passed through a hydrophobic frit. The residue was purified by silica gel column chromatography, eluting with DCM/10% MeOH in DCM (100/0 to 0/100), to give the title compound (MS (ESCI): m/z=216 (M+H)$^+$) as a mixture with 2-(4-nitro-1H-pyrazol-1-yl)ethanol.

Step 3—4,4-dimethyl-3-nitro-6,7-dihydro-4H-pyrazolo[5,1-c][1,4]oxazine

The product mixture from step 2 was dissolved in DCM (35 mL) was added DMAP (6 mg, 0.05 mmol), followed by a solution of tosyl chloride (801 mg, 4.2 mmol) in DCM (5 mL). The mixture was cooled to 0° C. and then triethylamine (2.6 mL, 18.4 mmol) added. The mixture was stirred at room temperature for 3 h and then water (50 mL) was added. The organic phase was passed through a hydrophobic frit and the solvent was removed in vacuo. The residue was dissolved in THF (200 mL) and sodium hydride (147 mg, 60% in oil, 3.68 mmol) was added. The mixture was stirred at room temperature for 24 h. Water (200 mL) and DCM (200 mL) were added and the organic phase was passed through a hydrophobic frit.

The solvent was removed in vacuo and the residue was purified by silica gel column chromatography, eluting with isohexane/ethyl acetate (100/0 to 0/100), to give the title compound (52 mg, 7% over three steps) as a yellow solid. $^1$H NMR (400 MHz, CDCl$_3$) δ 8.13 (s, 1H), 4.21-4.17 (m, 2H), 4.13-4.09 (m, 2H), 1.75 (s, 6H). LC-MS (ESCI): m/z=198 (M+H)$^+$.

Step 4—4,4-dimethyl-6,7-dihydro-4H-pyrazolo[5,1-c][1,4]oxazin-3-amine

To a solution of 4,4-dimethyl-3-nitro-6,7-dihydro-4H-pyrazolo[5,1-c][1,4]oxazine (52 mg, 0.26 mmol) in a mixture of ethanol (10 mL) and ethyl acetate (5 mL) was added palladium on carbon (25 mg, 10 wt %). The mixture was degassed with nitrogen and shaken under a hydrogen atmosphere (30 psi) for 18 h. The mixture was filtered through celite and the celite washed with ethanol. The solvent was removed in vacuo to give the title compound (44 mg, quant.) as an off-white solid. $^1$H NMR (400 MHz, CDCl$_3$) δ 7.13 (s, 1H), 4.06 (s, 4H), 2.62 (br s, 2H), 1.57 (s, 6H). LC-MS (ESCI): m/z=168 (M+H)$^+$.

Intermediate 13

6,7-dihydro-4H-pyrazolo[5,1-c][1,4]oxazin-2-amine

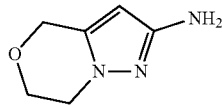

The title compound was prepared according to the procedure described in WO 2011/112995.

Intermediate 14

5-methyl-4,5,6,7-tetrahydropyrazolo[1,5-a]pyrazin-2-amine

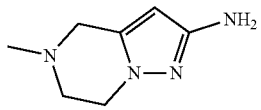

The title compound was prepared according to the procedure described in WO 2012/020008.

Intermediate 15

1-methyl-2,3-dihydro-1H-imidazo[1,2-b]pyrazol-7-amine

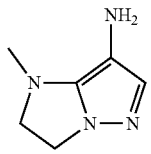

Step 1—7-nitro-2,3-dihydro-1H-imidazo[1,2-b]pyrazole

7-Nitro-2,3-dihydro-1H-imidazo[1,2-b]pyrazole was prepared according to the procedure described in WO2004/039814

Step 2—1-methyl-7-nitro-2,3-dihydro-1H-imidazo[1,2-b]pyrazole

To a solution of 7-nitro-2,3-dihydro-1H-imidazo[1,2-b]pyrazole (140 mg, 0.91 mmol) in THF (10 mL) was added sodium hydride (110 mg, 2.73 mmol). The resulting mixture was stirred for 30 min and then iodomethane (0.125 mL, 2 mmol) was added. The reaction was stirred at room temperature for 36 h and then quenched with water (10 mL). The THF was removed under reduced pressure and then the residue was taken up in DCM and washed with water. The aqueous phase was extracted with DCM (×3). The combined organic fractions were dried over magnesium sulfate, filtered and concentrated in vacuo to afford the title compound (150 mg, 99%). $^1$H NMR (400 MHz, CDCl3) δ 7.82 (s, 1H), 4.19 (t, J=7.2 Hz, 2H), 3.97 (t, J=7.2 Hz, 2H), 3.34 (s, 3H).

Step 3—1-methyl-2,3-dihydro-1H-imidazo[1,2-b]pyrazol-7-amine

To a solution of 1-methyl-7-nitro-2,3-dihydro-1H-imidazo[1,2-b]pyrazole (150 mg, 0.89 mmol) in ethanol (15 mL) was added palladium on carbon (20 mg, 10 wt %). The mixture was degassed with nitrogen and stirred under a hydrogen atmosphere (1 atm) for 18 h. The reaction mixture was filtered through celite and the celite washed with methanol. The solvent was removed in vacuo to give the title compound (120 mg, 98%). $^1$H NMR (400 MHz, CDCl3) δ 7.27 (s, 1H), 4.05 (t, J=7.6 Hz, 2H), 3.62 (t, J=7.6 Hz, 2H), 2.91 (s, 3H), 2.22 (br s, 2H).

Example 1

N2-(6,6-dimethyl-6,7-dihydro-4H-pyrazolo[5,1-c][1,4]oxazin-3-yl)-N4-methyl-5-(trifluoromethyl)pyrimidine-2,4-diamine

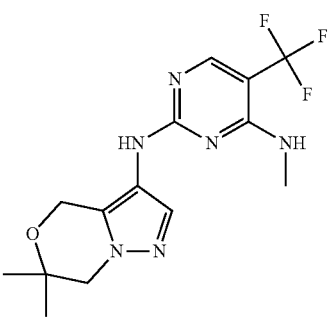 [SMILES: CNc1nc(Nc2cnn3c2COC(C)(C)C3)ncc1C(F)(F)F]

A microwave vial equipped with a magnetic stirrer was charged with 6,6-dimethyl-6,7-dihydro-4H-pyrazolo[5,1-c][1,4]oxazin-3-amine (13 mg, 0.078 mmol), 2-chloro-N-methyl-5-(trifluoromethyl)pyrimidin-4-amine (20 mg, 0.095 mmol), and t-BuOH (0.5 mL). The mixture was heated at 100° C. under microwave irradiation for 15 min. After concentration, the residue was purified by prep-HPLC to give the title compound (9.5 mg, 36%). $^1$H NMR (500 MHz, CDCl$_3$)

δ 8.09 (s, 1H), 7.67 (s, 1H), 6.79 (s, 1H), 5.18 (s, 1H), 4.83 (s, 2H), 3.93 (s, 2H), 3.00 (d, J=4.5 Hz, 3H), 1.63 (s, 6H). LC-MS (Method B): m/z=343.3 (M+H)⁺, 4.77 min, 98.2% purity.

Example 2

N4-methyl-N2-(1-methyl-2,3-dihydro-1H-imidazo[1,2-b]pyrazol-7-yl)-5-(trifluoromethyl)pyrimidine-2,4-diamine

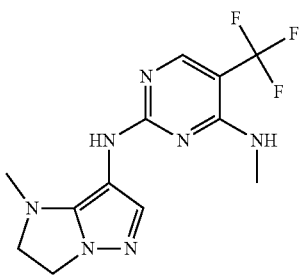 [SMILES: CNc1nc(Nc2cnn3c2N(C)CC3)ncc1C(F)(F)F]

A mixture of 1-methyl-2,3-dihydro-1H-pyrazolo[1,5-a]imidazol-7-amine (91 mg, 0.66 mmol), 2-chloro-N-methyl-5-(trifluoromethyl)pyrimidin-4-amine (90 mg, 0.44 mmol), cesium carbonate (287 mg, 0.88 mmol), palladium acetate (2 mg, 0.009) and Brettphos (7 mg, 0.013 mmol) in 1,4-dioxane (1.5 mL) was degassed by bubbling nitrogen through the mixture for 5 min. The reaction tube was sealed and the mixture was heated to 100° C. for 18 h. The mixture was cooled, diluted with ethyl acetate (5 mL) and washed with water (2×5 mL). The aqueous washes were combined and extracted with EtOAc (5 mL). The organic extracts were combined and filtered through a hydrophobic frit. The solvent was removed in vacuo and the residue was purified by preparative HPLC to give the title compound (19 mg, 14%). ¹H NMR (400 MHz, DMSO) δ 8.64† (br s, 1H), 8.32* (br s, 1H), 8.05 (s, 1H), 7.30† (br s, 1H), 7.11* (br s, 1H), 6.91 (s, 1H), 4.06 (t, J=7.6 Hz, 2H), 3.65 (t, J=7.6 Hz, 2H), 2.86 (d, J=4.4 Hz, 3H), 2.69 (s, 3H)† and * refer to different rotamers (arbitrarily assigned). LC-MS (Method C): m/z=314 (M+H)⁺, 2.78 min, 98.7% purity.

Compounds made using the above procedures are shown in Table 2 below, together with low resolution mass spectrometry (M+H), proton NMR, and LRRK2 K, (micromolar) data for selected compounds determined from the assay described below.

TABLE 2

| Name | Structure | ¹H NMR | M + H⁺ | K$_I$ |
|---|---|---|---|---|
| 3 N4-methyl-N2-(4,5,6,7-tetrahydropyrazolo[1,5-a]pyridin-3-yl)-5-(trifluoromethyl)pyrimidine-2,4-diamine | | | 313.2 | 0.0075 |
| 4 N2-(6,6-dimethyl-6,7-dihydro-4H-pyrazolo[5,1-c][1,4]oxazin-3-yl)-N4-ethyl-5-(trifluoromethyl)pyrimidine-2,4-diamine | | ¹H NMR (500 MHz, CDCl₃) δ 8.09 (s, 1 H), 7.61 (s, 1H), 6.66 (s, 1 H), 5.06 (s, 1 H), 4.82 (s, 2 H), 3.95 (s, 2 H), 3.48 (q, J = 7.0 Hz, 2 H), 1.38 (s, 6 H), 1.22 (t, J = 5.5 Hz, 3H). | 357.3 | |
| 5 (S)-N2-(4,5-dimethyl-4,5,6,7-tetrahydropyrazolo[1,5-a]pyrazin-3-yl)-N4-methyl-5-(trifluoromethyl)pyrimidine-2,4-diamine | | ¹H NMR (500 MHz, CDCl₃) δ 8.10 (s, 1H), 7.66 (s, 1H), 6.49 (s, 1H), 5.15 (s, 1H), 4.20-4.17 (m, 2H), 3.77 (q, J = 7 Hz, 1H), 3.22-3.18 (m, 1H), 3.01 (d, J = 4.5 Hz, 3H), 2.90-2.88 (m, 1H), 2.51 (s, 3H), 1.37 (d, J = 7.0 Hz, 3H). | 342.1 | 0.020 |

TABLE 2-continued

| Name | Structure | $^1$H NMR | M + H$^+$ | K$_I$ |
|---|---|---|---|---|
| 6 (R)-N2-(4,5-dimethyl-4,5,6,7-tetrahydropyrazolo[1,5-a]pyrazin-3-yl)-N4-methyl-5-(trifluoromethyl)pyrimidine-2,4-diamine | | $^1$H NMR (500 MHz, CDCl$_3$) δ 8.10 (s, 1H), 7.66 (s, 1H), 6.49 (s, 1H), 5.15 (s, 1H), 4.20-4.17 (m, 2H), 3.77 (q, J = 7 Hz, 1H), 3.22-3.18 (m, 1H), 3.01 (d, J = 4.5 Hz, 3H), 2.90-2.88 (m, 1H), 2.51 (s, 3H), 1.37 (d, J = 7.0 Hz, 3H). | | 0.184 |
| 7 (S)-N2-(4,5-dimethyl-4,5,6,7-tetrahydropyrazolo[1,5-a]pyrazin-3-yl)-N4-ethyl-5-(trifluoromethyl)pyrimidine-2,4-diamine | | $^1$H NMR (500 MHz, CDCl$_3$) δ 8.10 (s, 1H), 7.64 (s, 1H), 6.46 (s, 1H), 5.07 (s, 1H), 4.20-4.17 (m, 2H), 3.75 (q, J = 7 Hz, 1H), 3.51-3.48 (m, 2H), 3.22-3.19 (m, 1H), 2.90-2.87 (m, 1H), 2.51 (s, 3H), 1.38 (d, J = 7 Hz, 3H), 1.24 (t, J = 7 Hz, 3H). | | 0.0095 |
| 8 (R)-N2-(4,5-dimethyl-4,5,6,7-tetrahydropyrazolo[1,5-a]pyrazin-3-yl)-N4-ethyl-5-(trifluoromethyl)pyrimidine-2,4-diamine | | $^1$H NMR (500 MHz, CDCl$_3$) δ 8.10 (s, 1H), 7.64 (s, 1H), 6.46 (s, 1H), 5.07 (s, 1H), 4.20-4.17 (m, 2H), 3.75 (q, J = 7 Hz, 1H), 3.51-3.48 (m, 2H), 3.22-3.19 (m, 1H), 2.90-2.87 (m, 1H), 2.51 (s, 3H), 1.38 (d, J = 7 Hz, 3H), 1.24 (t, J = 7 Hz, 3H). | | 0.144 |
| 9 (S)-N4-cyclopropyl-N2-(4,5-dimethyl-4,5,6,7-tetrahydropyrazolo[1,5-a]pyrazin-3-yl)-5-(trifluoromethyl)pyrimidine-2,4-diamine | | $^1$H NMR (500 MHz, CDCl$_3$) δ 8.11 (s, 1H), 7.95 (s, 1H), 6.49 (s, 1H), 5.28 (s, 1H), 4.19-4.17 (m, 2H), 3.78 (s, 1H), 3.21-3.19 (m, 1H), 2.87-2.85 (m, 2H), 2.51 (s, 3H), 1.39 (d, J = 7.0 Hz, 3H), 0.86-0.84 (m, 2H), 0.59-0.58 (m, 2H). | 368.2 | 0.0049 |
| 10 (R)-N4-cyclopropyl-N2-(4,5-dimethyl-4,5,6,7-tetrahydropyrazolo[1,5-a]pyrazin-3-yl)-5-(trifluoromethyl)pyrimidine-2,4-diamine | | $^1$H NMR (500 MHz, CDCl$_3$) δ 8.11 (s, 1H), 7.95 (s, 1H), 6.49 (s, 1H), 5.28 (s, 1H), 4.19-4.17 (m, 2H), 3.78 (s, 1H), 3.21-3.19 (m, 1H), 2.87-2.85 (m, 2H), 2.51 (s, 3H), 1.39 (d, J = 7.0 Hz, 3H), 0.86-0.84 (m, 2H), 0.59-0.58 (m, 2H). | 368.2 | 0.0444 |
| 11 N4-methyl-5-(trifluoromethyl)-N2-(4,7,7-trimethyl-6,7-dihydro-4H-pyrazolo[5,1-c][1,4]oxazin-3-yl)pyrimidine-2,4-diamine | | | 357.1 | 0.212 |

TABLE 2-continued

| Name | Structure | ¹H NMR | M + H⁺ | K$_I$ |
|---|---|---|---|---|
| 12 N4-methyl-5-(trifluoromethyl)-N2-(4,7,7-trimethyl-6,7-dihydro-4H-pyrazolo[5,1-c][1,4]oxazin-3-yl)pyrimidine-2,4-diamine (enantiomer of Example 10) | | | 357.1 | 0.0026 |
| 13 N4-ethyl-N2-(4-methyl-6,7-dihydro-4H-pyrazolo[5,1-c][1,4]oxazin-3-yl)-5-(trifluoromethyl)pyrimidine-2,4-diamine | | | 343.1 | 0.0477 |
| 14 N4-ethyl-N2-(4-methyl-6,7-dihydro-4H-pyrazolo[5,1-c][1,4]oxazin-3-yl)-5-(trifluoromethyl)pyrimidine-2,4-diamine (enantiomer of Example 12) | | | 343.1 | 0.0012 |
| 15 N4-methyl-N2-(4-methyl-6,7-dihydro-4H-pyrazolo[5,1-c][1,4]oxazin-3-yl)-5-(trifluoromethyl)pyrimidine-2,4-diamine | | | | 0.279 |

TABLE 2-continued

| | Name | Structure | ¹H NMR | M + H⁺ | K$_I$ |
|---|---|---|---|---|---|
| 16 | N4-methyl-N2-(4-methyl-6,7-dihydro-4H-pyrazolo[5,1-c][1,4]oxazin-3-yl)-5-(trifluoromethyl)pyrimidine-2,4-diamine (enantiomer of Example 14) | 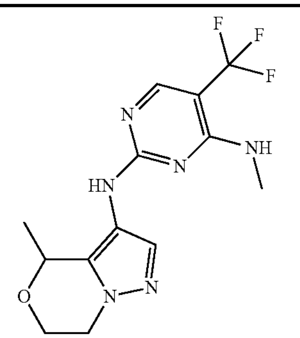 | ¹H NMR (400 MHz, DMSO) δ 8.80 (d, 1H), 8.05 (s, 1H), 7.40 (d, 1H), 6.92 (s, 1H), 4.96 (s, 1H), 4.06 (m, 1H), 4.04 (m, 2H), 3.86 (m, 1H), 2.83 (s, 3H), 1.30 (s, 3H) | 329.0 | 0.0030 |
| 17 | N2-(6,7-dihydro-4H-pyrazolo[5,1-c][1,4]oxazin-3-yl)-N4-methyl-5-(trifluoromethyl)pyrimidine-2,4-diamine | 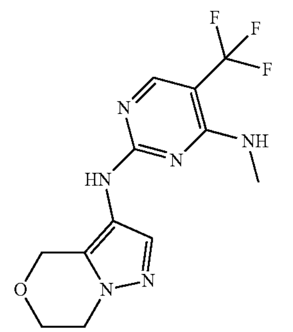 [SMILES: CNc1nc(Nc2cnn3c2COCC3)ncc1C(F)(F)F] | | | 0.0023 |
| 18 | N2-(4,6-dimethyl-6,7-dihydro-4H-pyrazolo[5,1-c][1,4]oxazin-3-yl)-N4-methyl-5-(trifluoromethyl)pyrimidine-2,4-diamine | 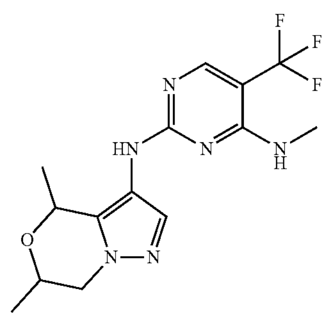 [SMILES: CNc1nc(Nc2cnn3c2C(C)OC(C)C3)ncc1C(F)(F)F] | ¹H NMR (400 MHz, DMSO) δ 8.96-8.62 (m, 1H), 8.05 (s, 1H), 7.63-7.25 (m, 1H), 6.91 (s, 1H), 4.88 (s, 1H), 4.11 (dd, J = 12.2, 2.8 Hz, 1H), 4.04-3.93 (m, 1H), 3.69 (t, J = 11.3 Hz, 1H), 2.81 (s, 3H), 1.37-1.21 (m, 6H). | 343.1 | 0.0018 |
| 19 | N2-(4,6-dimethyl-6,7-dihydro-4H-pyrazolo[5,1-c][1,4]oxazin-3-yl)-N4-methyl-5-(trifluoromethyl)pyrimidine-2,4-diamine (enantiomer of Example 17) | 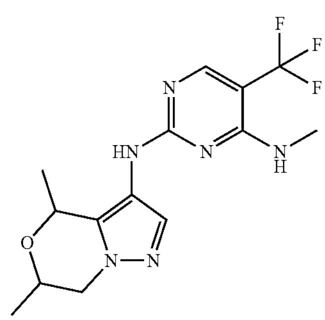 [SMILES: CNc1nc(Nc2cnn3c2C(C)OC(C)C3)ncc1C(F)(F)F] | ¹H NMR (400 MHz, DMSO) δ 9.08-8.58 (m, 1H), 8.06 (s, 1H), 7.82-7.33 (m, 1H), 6.95 (s, 1H), 5.31 (s, 1H), 4.30-4.16 (m, 1H), 4.09 (dd, J = 12.4, 3.2 Hz, 1H), 3.64 (dd, J = 12.4, 9.5 Hz, 1H), 2.85 (s, 3H), 1.31 (d, J = 5.7 Hz, 3H), 1.25 (d, J = 6.2 Hz, 3H). | 343.1 | 0.0613 |
| 20 | N2-(4,6-dimethyl-6,7-dihydro-4H-pyrazolo[5,1-c][1,4]oxazin-3-yl)-N4-methyl-5-(trifluoromethyl)pyrimidine-2,4-diamine (enantiomer of Example 17) | 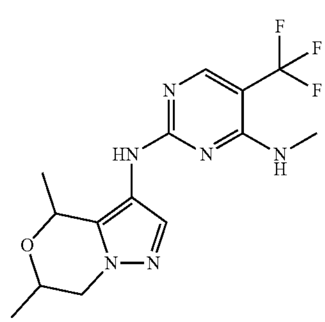 [SMILES: CNc1nc(Nc2cnn3c2C(C)OC(C)C3)ncc1C(F)(F)F] | ¹H NMR (400 MHz, DMSO) δ 9.10-8.57 (m, 1H), 8.06 (s, 1H), 7.81-7.34 (m, 1H), 6.95 (s, 1H), 5.31 (s, 1H), 4.29-4.18 (m, 1H), 4.09 (dd, J = 12.4, 3.1 Hz, 1H), 3.64 (dd, J = 12.3, 9.5 Hz, 1H), 2.85 (s, 3H), 1.31 (d, J = 5.6 Hz, 3H), 1.25 (d, J = 6.2 Hz, 3H). G02636122 382-D | 343.1 | 0.0057 |

TABLE 2-continued

| | Name | Structure | ¹H NMR | M + H⁺ | $K_I$ |
|---|---|---|---|---|---|
| 21 | N2-(4,6-dimethyl-6,7-dihydro-4H-pyrazolo[5,1-c][1,4]oxazin-3-yl)-N4-methyl-5-(trifluoromethyl)pyrimidine-2,4-diamine (enantiomer of Example 17) | 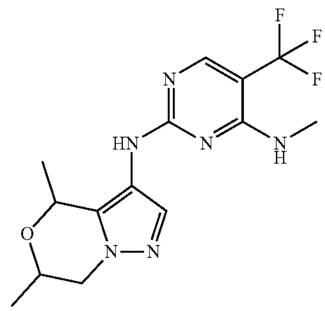 [SMILES: CNc1nc(Nc2cnn3c2C(C)OC(C)C3)ncc1C(F)(F)F] | ¹H NMR (400 MHz, DMSO) δ 8.97-8.60 (m, 1H). 8.05 (s, 1H), 7.65-7.25 (m, 1H), 6.92 (s, 1H), 4.88 (s, 1H), 4.11 (dd, J = 12.1, 2.7 Hz, 1H), 3.98 (s, 1H), 3.69 (t, J = 11.4 Hz, 1H), 2.82 (s, 3H), 1.39-1.21 (m, 6H). | 343.1 | 0.39 |
| 22 | N2-(6,6-dimethyl-6,7-dihydro-4H-pyrazolo[5,1-c][1,4]oxazin-3-yl)-N4-methyl-5-(trifluoromethyl)pyrimidine-2,4-diamine (enantiomer of Example 1) | 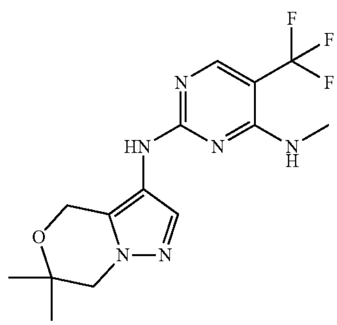 [SMILES: CNc1nc(Nc2cnn3c2COC(C)(C)C3)ncc1C(F)(F)F] | | | 0.0009 |
| 23 | N2-(6,6-dimethyl-6,7-dihydro-4H-pyrazolo[5,1-c][1,4]oxazin-3-yl)-N4-ethyl-5-(trifluoromethyl)pyrimidine-2,4-diamine (enantiomer of Example 3) | 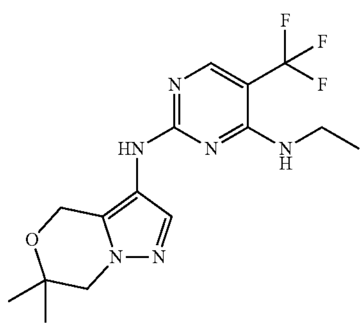 [SMILES: CCNc1nc(Nc2cnn3c2COC(C)(C)C3)ncc1C(F)(F)F] | | | 0.0003 |
| 24 | N2-(5,6-dihydro-4H-pyrrolo[1,2-b]pyrazol-3-yl)-N4-methyl-5-(trifluoromethyl)pyrimidine-2,4-diamine | 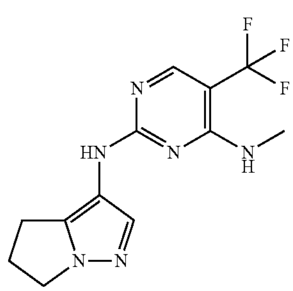 [SMILES: CNc1nc(Nc2cnn3c2CCC3)ncc1C(F)(F)F] | ¹H NMR (400 MHz, DMSO) δ 9.25-9.10 (m, 1H), 8.06 (s, 1H), 6.91 (s, 2H), 4.01 (t, J = 7.2 Hz, 2H), 2.86 (dd, J = 13.3, 6.0 Hz, 4H), 2.47 (s, 2H). | 299.1 | 0.0006 |
| 25 | N4-methyl-N2-(1-methyl-2,3-dihydro-1H-imidazo[1,2-b]pyrazol-7-yl)-5-(trifluoromethyl)pyrimidine-2,4-diamine | 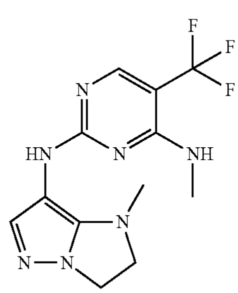 [SMILES: CNc1nc(Nc2cnn3c2N(C)CC3)ncc1C(F)(F)F] | ¹H NMR (400 MHz, DMSO) δ 8.64† (br s, 1H), 8.32* (br s, 1H), 8.05 (s, 1H), 7.30† (br s, 1H), 7.11* (br s, 1H), 6.91 (s, 1H),4.06 (t, J = 7.6 Hz, 2H), 3.65 (t, J = 7.6 Hz, 2H), 2.86 (d, J = 4.4 Hz, 3H), 2.69 (s, 3H)† and * refer to different rotamers (arbitrarily assigned). | 314 | 0.0312 |

| | Name | Structure | ¹H NMR | M + H⁺ | K$_I$ |
|---|---|---|---|---|---|
| 26 | N⁴-methyl-N²-(5-methyl-4,5,6,7-tetrahydropyrazolo[1,5-a]pyrazin-3-yl)-5-(trifluoromethyl)pyrimidine-2,4-diamine | 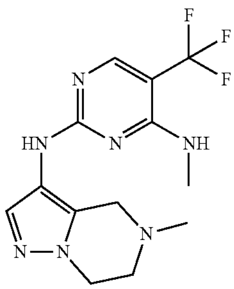 [SMILES: CNc1nc(Nc2cnn3c2CN(C)CC3)ncc1C(F)(F)F] | ¹H NMR (400 MHz, CD3OD) δ 7.95 (s, 1H), 7.69 (br s, 1H), 4.15-3.95 (m, 2H), 3.62 (s, 2H), 3.01-2.85 (m, 5H), 2.53 (s, 3H). | 328 | 0.0335 |
| 27 | N²-(6'7'-dihydrospiro[oxetane-3,4'-pyrazolo[5,1-c][1,4]oxazine]-3-yl)-N⁴-methyl-5-(trifluoromethyl)pyrimidine-2,4-diamine | 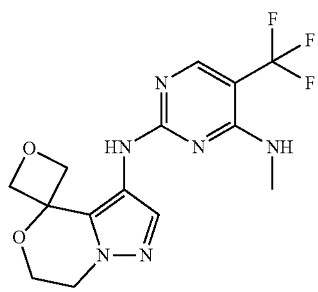 [SMILES: CNc1nc(Nc2cnn3c2C2(COC2)OCC3)ncc1C(F)(F)F] | ¹H NMR (400 MHz, CDCl₃) δ 8.20 (br s, 1H), 8.14 (s, 1H), 7.88 (br s, 1H), 5.21 (br s, 1H), 4.99 (d, J = 6.6 Hz, 2H), 4.89 (d, J = 6.6 Hz, 2H), 4.16 (dd, J = 5.7, 4.3 Hz, 2H), 4.04 (dd, J = 5.7, 4.3 Hz, 2H), 3.10 (d, J = 4.7 Hz, 3H). | 357 | 0.8189 |
| 28 | N²-(4,4-dimethyl-6,7-dihydro-4H-pyrazolo[5,1-c][1,4]oxazin-3-yl)-N⁴-methyl-5-(trifluoromethyl)pyrimidine-2,4-diamine | 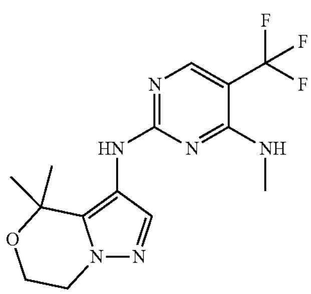 [SMILES: CNc1nc(Nc2cnn3c2C(C)(C)OCC3)ncc1C(F)(F)F] | ¹H NMR (400 MHz, CDCl₃) δ 8.09 (s, 1H), 7.67 (br s, 1H), 6.15 (br s, 1H), 5.14 (br s, 1H), 4.16-4.08 (m, 4H), 2.99 (d, J = 4.7 Hz, 3H), 1.56 (s, 6H). | 343 | |
| 29 | N⁴-methyl-N²-(5-methyl-4,5,6,7-tetrahydropyrazolo[1,5-a]pyrazin-2-yl)-5-(trifluoromethyl)pyrimidine-2,4-diamine | 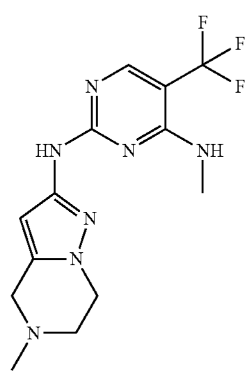 [SMILES: CNc1nc(Nc2cc3n(n2)CCN(C)C3)ncc1C(F)(F)F] | ¹H NMR (400 MHz, CDCl₃) δ 8.17 (s, 1H), 7.52 (br s, 1H), 6.49 (s, 1H), 5.17 (br s, 1H), 4.09 (t, J = 5.6 Hz, 2H), 3.64 (s, 2H), 3.08 (d, J = 4.8 Hz, 3H), 2.89 (t, J = 5.6 Hz, 2H), 2.49 (s, 3H). | 328 | |
| 30 | N²-(6,7-dihydro-4H-pyrazolo[5,1-c][1,4]oxazin-2-yl)-N⁴-methyl-5-(trifluoromethyl)pyrimidine-2,4-diamine | 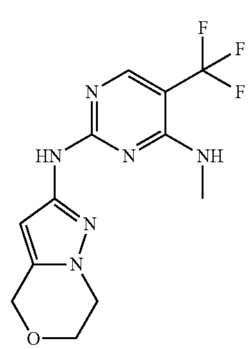 [SMILES: CNc1nc(Nc2cc3n(n2)CCOC3)ncc1C(F)(F)F] | ¹H NMR (400 MHz, CDCl₃) δ 8.18 (s, 1H), 7.82 (br s, 1H), 6.54 (s, 1H), 5.30 (br s, 1H), 4.83 (s, 2H), 4.14-4.05 (m, 4H), 3.08 (d, J = 4.4 Hz, 3H). | 315 | 0.0109 |

Example 31

In Vitro LRRK2 Lanthascreen Binding Assay

This assay was used to determine a compound's potency in inhibiting activity of LRRK2 by determining, $Ki_{app}$, $IC_{50}$, or percent inhibition values. In 384 well proxiplates F black, shallow well plates LRRK2, Eu-anti-GST-antibody, Alexa Fluor® Kinase tracer 236 and test compound were incubated together.

Binding of the Alexa Fluor® "tracer" to a kinase is detected by addition of a Eu-labeled anti-GST antibody. Binding of the tracer and antibody to a kinase results in a high degree of FRET, whereas displacement of the tracer with a kinase inhibitor results in a loss of FRET.

Assay conditions and materials used were as follows:
Final Assay Conditions:
GST-LRRK2 G2019S 10 nM
Eu-anti-GST-antibody 2 nM
Kinase tracer 236 8.5 nM
Kinase reaction time: 1 hour
Temperature: ambient
Total volume: 15 µl
DMSO 1%
Materials:
384 well proxiplates F black shallow well Perkin Elmer cat #6008260
Kinase: LRRK2 G2019S, Invitrogen cat # PV4882 (LOT 567054A).
Eu-labeled anti-GST antibody Invitrogen cat # PV5594
Alexa Fluor® Kinase tracer 236 Invitrogen cat #PV5592
TRIS-HCl Sigma cat # T3253
EGTA Sigma cat # E3889
Brij-35: Sigma cat # B4184 (30% w/v)
DMSO: Sigma cat # D8418
$MgCl_2$ Sigma cat # M9272
Reaction Buffer: $H_2O$/50 mM Tris, pH 7.4/10 mM $MgCl_2$/1 mM EGTA/0.01% Brij 35
Compound Plate Preparation:
Serially dilute test compounds (10 mM stock) 1:3.16 (20 ul+43.2 ul) in 100% DMSO. 12 pt curve. Dilute each concentration 1:33.3 (3 ul+97 ul) in reaction buffer. Stamp 5 ul to assay plate. Final top test concentration 100 uM
Total and Blank Preparation:
In Reaction Buffer, 5 ul of DMSO (3%) was added to total and blank wells and 5 ul of Eu-labeled anti-GST antibody (6 nM) was added to blank wells. Add 5 ul LRRK2 (30 nM)/Eu-labeled anti-GST antibody (6 nM) mix to compound and total wells.
Assay Procedure:
Add 5 ul kinase tracer (25.5 nM) to all wells. Incubate plates at room temperature for 1 hour on a plate shaker (gentle shaking). Read on Perkin Elmer EnVision reader HTRF protocol
Data Handling:
Calculate ratio: (665/620)*10000. Subtract mean background values from all data points. Calculate % of control for each test value. Plot % of control vs Compound concentration. Calculate Ki Value (xlfit curve fitting—Morrison equation). Results expressed as a Ki in µM. Equation for Ki:

$$Y=V0*(1-((x+Ki*(1+S/Km)+Et)/(2*Et)-(((x+Ki*(1+S/Km)+Et)^2-(4*Et*x))^0.5)/(2*Et)))$$

Where Et=4 nM
kd (Tracer)=8.5 nM
Tracer concentration (S)=8.5 nM

Example 32

In Vitro LRRK2 Assay

This assay was used to determine a compound's potency in inhibiting activity of LRRK2 by determining, $Ki_{app}$, $IC_{50}$, or percent inhibition values. In a polypropylene plate, LRRK2, fluorescently-labeled peptide substrate, ATP and test compound were incubated together. Using a LabChip 3000 (Caliper Life Sciences), after the reaction the substrate was separated by capillary electrophoresis into two populations: phosphorylated and unphosphorylated. The relative amounts of each were quantitated by fluorescence intensity. LRRK2 Ki was determined according to the equation:

$$Y=V0*(1-((x+Ki*(1+S/Km)+Et)/(2*Et)-(((x+Ki*(1+S/Km)+Et)^2-(4*Et*x))^0.5)/(2*Et))).$$

Ki values in Table 4 and elsewhere herein are shown in µM.
Assay conditions and materials used were as follows:
Final Assay Conditions:
LRRK2 G2019S in 5 mM $MgCl_2$: 5.2 nM (Invitrogen lot #567054A)
LRRK2 G2019S in 1 mM $MnCl_2$: 11 nM (Invitrogen lot #567054A)
LRRK2 Wild type in 5 mM $MgCl_2$: 15 nM (Invitrogen lot #500607F)
LRRK2 I2020T in 5 mM $MgCl_2$: 25 nM (Invitrogen lot #43594)
Substrate: 1 µM
ATP: 130 µM
Kinase reaction time: 2 hours
Temperature: ambient
Total volume: 20 µl
$ATP^{app}$ Kms:
G2019S in 5 mM $MgCl_2$: 130 µM
G2019S in 1 mM $MnCl_2$: 1 µM
Wild type in 5 mM $MgCl_2$: 80 µM
I2020T in 5 mM $MgCl_2$: 14 µM
Materials:
Solid Support: Black 50 µL volume polypropylene 384 well plate (MatriCal cat # MP101-1-PP)
Kinase: LRRK2 G2019S (Invitrogen cat # PV4882). LRRK2 Wild type (Invitrogen cat # PV4874).
Substrate: 5FAM-GAGRLGRDKYKTLRQIRQ-$CONH_2$
Non-binding plate: 384 well clear V-bottom polypropylene plates (Greiner cat #781280).
ATP: 10 mM ATP (Cell Signaling cat #9804).
Triton X-100: Triton X-100.
Brij-35: Brij-35 (Pierce cat #20150).
Coating Reagent #3: Coating Reagent #3 (Caliper).
DMSO: DMSO (Sigma cat #34869-100 ML).
Complete Reaction Buffer: $H_2O$/25 mM Tris, pH 8.0/5 mM $MgCl_2$/2 mM DTT/0.01% Triton X-100.
Stop Solution: $H_2O$/100 mM HEPES, pH 7.2/0.015% Brij-35/0.2% Coating Reagent #3/20 mM EDTA.
Separation Buffer: $H_2O$/100 mM HEPES, pH 7.2/0.015% Brij-35/0.1% Coating Reagent #3/1:200 Coating Reagent #8/10 mM EDTA/5% DMSO.
Compound Plate Preparation:
For serial dilutions, 34.6 µl DMSO was added to columns 3-24. For the assay controls, 37.5 µl DMSO was added to columns 1 and 2 of rows A and P. a,d and 50 µl 25 µM G-028831 (Staurosporine) was added to columns 1 and 2, row B. For the samples: start at 100 µM, 37.5 µl DMSO was to columns 1 and 2, then 12.5 µl 10 mM compound; to start at 10 µM, 78 µl DMSO was added to columns 1 & 2, then 2 µl 10 mM compound; and to start at 1 μM, 25 μM compound (2 μl 10 mM cmpd+798 μl DMSO) was added to empty columns 1 and 2. A Precision instrument was used to perform 1:3.16 serial dilutions ("PLK_BM_serial_halflog").

ATP Preparation:
ATP was diluted to 282.1 μM in Complete Kinase Buffer (final concentration was 130 μm).

Total and Blank Preparation:
In Complete Reaction Buffer, substrate was diluted to 4 μM. Equal volumes of Complete Reaction Buffer and 4 μM substrate were combined to obtain the blank. Equal volumes of Complete Reaction Buffer and 4 μM substrate were combined and to the combined solution was added 2× final LRRK2 concentration.

Assay Procedure:
To a 50 μl polypropylene plate, 5 μl/well buffer/substrate was added by hand to Blank wells. A Biomek FX was used to start the kinase reaction ("PLK SAR 23 ATP"). The following were added to the appropriate wells:
  2 μl compound+23 μl ATP;
  5 μl/well compound/ATP in Assay Plate;
  5 μl/well kinase/substrate in Assay Plate;
The plate was incubated for 2 hours in the dark. Biomek FX was used to stop the kinase reaction ("PLK Stop"), and 10 μl/well Stop solution was added to the Assay Plate. Results were read on the LabChip 3000.

Lab Chip 3000 Protocol:
The LabChip 3000 was run using the job "LRRK2 IC50" with the following job settings:
  Pressure: −1.4 psi
  Downstream voltage: −500 V
  Upstream voltage: −2350 V
  Post sample buffer sip time: 75 seconds
  Post dye buffer sip time: 75 seconds
  Final delay time: 200 seconds Example 33

Parkinson's Disease Mouse Model

Parkinson's disease can be replicated in mice and in primates by administration of 1-methyl-4-phenyul tetrahydropyridine (MPTP), a selective nigrostriatal dopaminergic neurotoxin that produces a loss of striatal dopamine (DA) nerve terminal markers. Compounds of the invention may be evaluated for effectiveness in treatment of Parkinson's disease using MPTP induced neurodegeneration following generally the protocol described by Saporito et al., *J. Pharmacology* (1999) Vol. 288, pp. 421-427.

Briefly, MPTP is dissolved in PBS at concentrations of 2-4 mg/ml, and mice (male C57 weighing 20-25 g) are given a subcutaneous injection of 20 to 40 mg/kg. Compounds of the invention are solubilized with polyethylene glycol hydroxystearate and dissolved in PBS. Mice are administered 10 ml/kg of compound solution by subcutaneous injection 4 to 6 h before MPTP administration, and then daily for 7 days. On the day of the last injection, mice are sacrificed and the midbrain blocked and postfixed in paraformaldehyde. Striata are dissected free, weighed, and stored at −70° C.

The striata thus collected are evaluated for content of dopamine and its metabolites dihydroxyphenylacetic acid and homovanillic acid, by HPLC with electrochemical detection as described by Sonsalla et al., *J. Pharmacol. Exp. Ther.* (1987) Vol. 242, pp. 850-857. The striata may also be evaluated using the tyrosine hydroxylase assay of Okunu et al., *Anal Biochem* (1987) Vol. 129, pp. 405-411 by measuring $^{14}CO_2$ evolution associated with tyrosine hydroxylase-mediated conversion of labeled tyrosine to L-dopa. The striata may further be evaluated using the Monoamine oxidase-B assay as described by White et al., *Life Sci.* (1984), Vol. 35, pp. 827-833, and by monitoring dopamine uptake as described by Saporito et al., (1992) Vol. 260, pp. 1400-1409.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula I:

or a pharmaceutically acceptable salt thereof,
wherein:
  X is: —$NR^a$—; or —O— wherein $R^a$ is hydrogen or $C_{1-6}$alkyl;
  $R^1$ is: methyl, ethyl or cyclopropyl
  $R^2$ is: halo; halo-$C_{1-6}$alkyl or cyano;
  $R^3$ is: hydrogen; $C_{1-6}$alkyl; halo; cyano; halo-$C_{1-6}$alkyl; $C_{2-6}$alkenyl; $C_{2-6}$alkynyl; $C_{1-6}$alkoxy; $C_{1-6}$alkoxy-$C_{1-6}$alkyl; hydroxy-$C_{1-6}$alkyl; $C_{3-6}$cycloalkyl optionally substituted one or more times with $R^4$; $C_{3-6}$cycloalkyl-$C_{1-6}$alkyl wherein the $C_{3-6}$cycloalkyl portion is optionally substituted one or more times with $R^4$; or —Y—C(O)—$R^d$;
  Y is $C_{2-6}$alkylene or a bond;
  $R^d$ is $C_{1-6}$alkyl, $C_{1-6}$alkoxy, amino, $C_{1-6}$alkyl-amino, di-$C_{1-6}$alkyl-amino, halo-$C_{1-6}$alkyl-amino, di-halo-$C_{1-6}$alkyl-amino, halo-$C_{1-6}$alkyl, hydroxy-$C_{1-6}$alkyl, hydroxy, $C_{1-6}$alkoxy-$C_{1-6}$alkyl, cyano-$C_{1-6}$alkyl, $C_{1-6}$alkylsulfonyl$C_{1-6}$alkyl, amino-$C_{1-6}$alkyl, $C_{3-6}$cycloalkyl optionally substituted one or more times with $R^4$, $C_{3-6}$cycloalkyl-$C_{1-6}$alkyl wherein the $C_{3-6}$cycloalkyl portion is optionally substituted one or more times with $R^4$, heterocyclyl selected from piperidinyl, pyrrolidinyl, oxetanyl, tetrahydropyranyl, tetrahydrofuranyl, azetidinyl, [1,3]dioxolanyl and tetrahydrothiopyranyl, each of which may be optionally substituted one or more times with $R^5$, or heterocyclyl-$C_{1-6}$alkyl wherein the heterocyclyl portion is selected from piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl, each of which may optionally substituted one or more times with $R^5$;
  each $R^4$ is independently: $C_{1-6}$alkyl; halo-$C_{1-6}$alkyl; $C_{1-6}$alkoxy; oxo; cyano; halo; or Y—C(O)—$R^d$;
  each $R^5$ is independently: $C_{1-6}$alkyl; halo-$C_{1-6}$alkyl; halo; oxo; $C_{1-6}$alkoxy; $C_{1-6}$alkylsulfonyl; $C_{1-6}$alkoxy-$C_{1-6}$ alkyl; cyano; —Y—C(O)—R$^d$; heterocyclyl selected from piperidinyl, pyrrolidinyl, oxetanyl, tetrahydropyranyl, tetrahydrofuranyl, azetidinyl, [1,3]dioxolanyl and tetrahydrothiopyranyl; heterocyclyl-C$_{1-6}$alkyl wherein the heterocyclyl moiety is selected from piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl; C$_{3-6}$cycloalkyl; C$_{3-6}$cycloalkyl-C$_{1-6}$alkyl; and C$_{3-6}$cycloalkylsulfonyl;

A is a five- or six-membered unsaturated or saturated carbocyclic ring that may may optionally contain a heteroatom selected from O, N and S, and which may be substituted one or more times with R$^6$; and each R$^6$ is independently: oxo; C$_{1-6}$alkyl; halo-C$_{1-6}$alkyl; C$_{1-6}$alkoxy; C$_{1-6}$alkoxy-C$_{1-6}$alkyl; cyano; cyano-C$_{1-6}$alkyl; —Y—C(O)—R$^d$; C$_{3-6}$cycloalkyl, oxetanyl; or C$_{3-6}$cyclo alkyl-C$_{1-6}$alkyl.

2. The compound of claim 1, wherein X is —NH—.

3. The compound of claim 1, wherein R$^3$ is hydrogen or C$_{1-6}$alkyl.

4. The compound of claim 1, wherein R$^4$ is C$_{1-6}$alkyl; halo-C$_{1-6}$alkyl; or halo.

5. The compound of claim 1, wherein R$^5$ is C$_{1-6}$alkyl; halo-C$_{1-6}$alkyl; or halo.

6. The compound of claim 1, wherein ring A is a five-membered ring.

7. The compound of claim 1, wherein ring A is a six-membered ring.

8. The compound of claim 1, wherein ring A is saturated.

9. The compound of claim 1, wherein ring A is carbocyclic.

10. The compound of claim 1, wherein ring A contains a heteroatom selected from O, N and S.

11. The compound of claim 1, wherein ring A is substituted at least once with a group R$^6$.

12. The compound of claim 1, wherein R$^6$ is C$_{1-6}$alkyl.

13. The compound of claim 1, wherein said compound is of formula IIA or formula IIB:

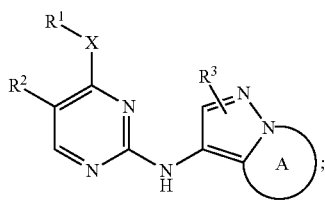

IIA

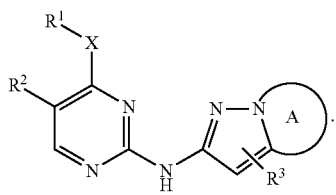

IIB

14. The compound of claim 1, wherein said compound is of formula III:

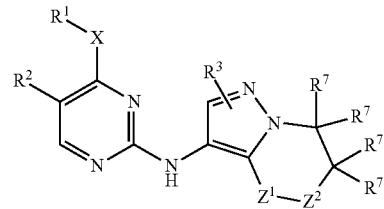

III wherein:
one of Z$^1$ and Z$^2$ is —O— or —NR$^7$— and the other is —C(R$^7$)$_2$—;
or both of Z$^1$ and Z$^2$ are —C(R$^7$)$_2$—;
or two of R$^7$ together with the atom or atoms to which they are attached may form a four to seven membered unsaturated ring that is carbocyclic or which includes a heteroatom selected from O, N and S; and
R$^1$, R$^2$ and R$^3$ are as recited in claim 1.

15. The compound of claim 1, wherein at least one of R$^7$ is C$_{1-6}$alkyl.

16. The compound of claim 1, wherein said compound is selected from:
N4-methyl-N2-(4,5,6,7-tetrahydropyrazolo[1,5-a]pyridin-3-yl)-5-(trifluoromethyl)pyrimidine-2,4-diamine;
N2-(6,6-dimethyl-6,7-dihydro-4H-pyrazolo[5,1-c][1,4]oxazin-3-yl)-N4-ethyl-5-(trifluoromethyl)pyrimidine-2,4-diamine;
(S)—N2-(4,5-dimethyl-4,5,6,7-tetrahydropyrazolo[1,5-a]pyrazin-3-yl)-N4-methyl-5-(trifluoromethyl)pyrimidine-2,4-diamine;
(R)—N2-(4,5-dimethyl-4,5,6,7-tetrahydropyrazolo[1,5-a]pyrazin-3-yl)-N4-methyl-5-(trifluoromethyl)pyrimidine-2,4-diamine;
(S)—N2-(4,5-dimethyl-4,5,6,7-tetrahydropyrazolo[1,5-a]pyrazin-3-yl)-N4-ethyl-5-(trifluoromethyl)pyrimidine-2,4-diamine;
(R)—N2-(4,5-dimethyl-4,5,6,7-tetrahydropyrazolo[1,5-a]pyrazin-3-yl)-N4-ethyl-5-(trifluoromethyl)pyrimidine-2,4-diamine;
(S)—N4-cyclopropyl-N2-(4,5-dimethyl-4,5,6,7-tetrahydropyrazolo[1,5-a]pyrazin-3-yl)-5-(trifluoromethyl)pyrimidine-2,4-diamine;
(R)—N4-cyclopropyl-N2-(4,5-dimethyl-4,5,6,7-tetrahydropyrazolo[1,5-a]pyrazin-3-yl)-5-(trifluoromethyl)pyrimidine-2,4-diamine;
N4-methyl-5-(trifluoromethyl)-N2-(4,7,7-trimethyl-6,7-dihydro-4H-pyrazolo[5,1-c][1,4]oxazin-3-yl)pyrimidine-2,4-diamine;
N4-ethyl-N2-(4-methyl-6,7-dihydro-4H-pyrazolo[5,1-c][1,4]oxazin-3-yl)-5-(trifluoromethyl)pyrimidine-2,4-diamine;
N4-methyl-N2-(4-methyl-6,7-dihydro-4H-pyrazolo[5,1-c][1,4]oxazin-3-yl)-5-(trifluoromethyl)pyrimidine-2,4-diamine;
N2-(6,7-dihydro-4H-pyrazolo[5,1-c][1,4]oxazin-3-yl)-N4-methyl-5-(trifluoromethyl)pyrimidine-2,4-diamine;
N2-(4,6-dimethyl-6,7-dihydro-4H-pyrazolo[5,1-c][1,4]oxazin-3-yl)-N4-methyl-5-(trifluoromethyl)pyrimidine-2,4-diamine;
N2-(6,6-dimethyl-6,7-dihydro-4H-pyrazolo[5,1-c][1,4]oxazin-3-yl)-N4-methyl-5-(trifluoromethyl)pyrimidine-2,4-diamine;
N2-(5,6-dihydro-4H-pyrrolo[1,2-b]pyrazol-3-yl)-N4-methyl-5-(trifluoromethyl)pyrimidine-2,4-diamine;

N4-methyl-N2-(1-methyl-2,3-dihydro-1H-imidazo[1,2-b]pyrazol-7-yl)-5-(trifluoromethyl)pyrimidine-2,4-diamine;

N2-methyl-N4-(5-methyl-4,5,6,7-tetrahydropyrazolo[1,5-a]pyrazin-3-yl)-5-(trifluoromethyl)pyrimidine-2,4-diamine;

N2-(6',7'-dihydrospiro[oxetane-3,4'-pyrazolo[5,1-c][1,4]oxazine]-3'-yl)-N4-methyl-5-(trifluoromethyl)pyrimidine-2,4-diamine;

N2-(4,4-dimethyl-6,7-dihydro-4H-pyrazolo[5,1-c][1,4]oxazin-3-yl)-N4-methyl-5-(trifluoromethyl)pyrimidine-2,4-diamine;

N4-methyl-N2-(5-methyl-4,5,6,7-tetrahydropyrazolo[1,5-a]pyrazin-2-yl)-5-(trifluoromethyl)pyrimidine-2,4-diamine; and N2-(6,7-dihydro-4H-pyrazolo[5,1-c][1,4]oxazin-2-yl)-N4-methyl-5-(trifluoromethyl)pyrimidine-2,4-diamine.

17. A composition comprising:
(a) a pharmaceutically acceptable carrier; and
(b) a compound of claim 1.

18. A method for treating Parkinson's disease, said method comprising administering to a subject in need thereof an effective amount of a compound of claim 1.

* * * * *